(12) United States Patent
Herrmann et al.

(10) Patent No.: US 10,463,891 B2
(45) Date of Patent: Nov. 5, 2019

(54) **EXTRACTS OF *ISOCHRYSIS* SP.**

(75) Inventors: Martina Herrmann, Hameln (DE); Holger Joppe, Dassel (DE); Paolo Pertile, San Pietro Viminario (IT); Lorenzo Zanella, Venezia-Mestre (IT)

(73) Assignee: Symrise AG, Holzminden (DE)

( * ) Notice: Subject to any disclaimer, the term of this patent is extended or adjusted under 35 U.S.C. 154(b) by 864 days.

(21) Appl. No.: 12/568,475

(22) Filed: Sep. 28, 2009

(65) Prior Publication Data
US 2010/0080761 A1 Apr. 1, 2010

Related U.S. Application Data

(60) Provisional application No. 61/101,228, filed on Sep. 30, 2008.

(51) Int. Cl.
*A61Q 19/04* (2006.01)
*A61Q 7/00* (2006.01)
*A61Q 7/02* (2006.01)
*A61Q 19/02* (2006.01)
*A61K 8/9706* (2017.01)

(52) U.S. Cl.
CPC ............ *A61Q 19/04* (2013.01); *A61K 8/9706* (2017.08); *A61Q 7/00* (2013.01); *A61Q 7/02* (2013.01); *A61Q 19/02* (2013.01)

(58) Field of Classification Search
CPC .......... A61K 8/975; A61C 7/00; A61C 19/04; A61C 19/02; A61C 7/02; C12N 1/12
See application file for complete search history.

(56) References Cited

U.S. PATENT DOCUMENTS

| | | | |
|---|---|---|---|
| 4,110,430 A | 8/1978 | Hopp et al. | |
| 4,251,195 A | 2/1981 | Suzuki et al. | |
| 5,620,962 A * | 4/1997 | Winget | A61K 9/0014 514/25 |
| 5,767,095 A | 6/1998 | Winget | |
| 6,139,852 A * | 10/2000 | Takeoka et al. | |
| 6,214,376 B1 | 4/2001 | Gennadios | |
| 6,465,421 B1 * | 10/2002 | Duranton et al. | |
| 2002/0041853 A1 * | 4/2002 | Ishii | A61K 8/29 424/59 |
| 2004/0049062 A1 * | 3/2004 | Bijl | A23D 9/00 554/1 |
| 2005/0069566 A1 * | 3/2005 | Tamarkin | A61K 8/046 424/401 |
| 2005/0129780 A1 * | 6/2005 | Holcomb-Halstead | A61K 31/19 424/551 |
| 2006/0089413 A1 | 4/2006 | Schmaus et al. | |
| 2006/0269497 A1 | 11/2006 | Okada | |
| 2008/0070825 A1 | 3/2008 | Bertram et al. | |

FOREIGN PATENT DOCUMENTS

| | | | | |
|---|---|---|---|---|
| DE | 4447361 A1 | 6/1996 | | |
| DE | 10143434 A1 | 3/2003 | | |
| DE | 10330697 A1 | 2/2005 | | |
| EP | 0389700 A1 | 10/1990 | | |
| EP | 0553884 A1 | 8/1993 | | |
| EP | 0584178 A1 | 3/1994 | | |
| EP | 0629397 A1 * | 12/1994 | ............... | A61K 8/97 |
| EP | 0671161 A1 | 9/1995 | | |
| EP | 918517 A1 | 6/1999 | | |
| EP | 1157687 A2 | 11/2001 | | |
| EP | 1745794 A2 | 1/2007 | | |
| EP | 1886679 A2 | 2/2008 | | |
| FR | 2657012 A1 | 7/1991 | | |
| FR | 2676454 A1 | 11/1992 | | |
| FR | 2801788 A1 | 6/2001 | | |
| JP | S62132808 A | 6/1987 | | |
| JP | H01186809 A | 7/1989 | | |
| JP | 7196478 A | 8/1995 | | |
| JP | 2002068943 A * | 3/2002 | | |
| JP | 2002068943 A * | 3/2002 | | |
| WO | WO-9415923 A2 | 7/1994 | | |
| WO | WO-9424984 A2 | 11/1994 | | |
| WO | WO-0176572 A2 | 10/2001 | | |
| WO | WO-0215868 A2 | 2/2002 | | |
| WO | WO-0238537 A1 | 5/2002 | | |
| WO | WO-03055587 A1 | 7/2003 | | |
| WO | WO-2004050069 A1 | 6/2004 | | |
| WO | WO-2005032501 A1 | 4/2005 | | |
| WO | WO-2005102252 A2 | 11/2005 | | |
| WO | WO-2005107692 A1 | 11/2005 | | |
| WO | WO-2005123101 A1 | 12/2005 | | |
| WO | WO-2006010661 A1 | 2/2006 | | |
| WO | WO-2006015954 A1 | 2/2006 | | |
| WO | WO-2006045760 A1 | 5/2006 | | |
| WO | WO-2006053912 A1 | 5/2006 | | |
| WO | WO-2006122299 A2 * | 11/2006 | ............. | A61K 31/20 |
| WO | WO-2007042472 A1 | 4/2007 | | |
| WO | WO-2007077541 A2 | 7/2007 | | |
| WO | WO-2007110415 A2 | 10/2007 | | |
| WO | WO-2008046676 A1 | 4/2008 | | |
| WO | WO-2008046791 A1 | 4/2008 | | |
| WO | WO-2008046795 A1 | 4/2008 | | |

OTHER PUBLICATIONS

Liu, C-P et al. (2001); Bot. Bull. Acad. Sin. 42: 207-214. Ultrastructural study and lipid *Isochrysis* sp. CCMP1324.*
http://www.straininfo.net/strains/810762/browser. CSIRO: Australian National Algae Culture Collection, ANACC Published Strains Database: "Culture CS-177". Downloaded from world-wide-web on Apr. 2, 2012.*
Grima et al. Comparision Between Extraction of Lipids and Fatty Acids From Microalgal Biomass; JAOCS, vol. 71, No. 9, 1994 pp. 955-959.*
Wingerter, K. *Isochrysis*: The Microalgal Reef Aquarium Superfood. [Retrieved on: Jan. 2, 2018]. Retrieved from the internet: <URL: https://www.algaebarn.com/isochrysis-the-microalgal-reef-aquarium-superfood/>. (Year: 2017).*

(Continued)

*Primary Examiner* — Amy L Clark
(74) *Attorney, Agent, or Firm* — Dilworth & Barrese LLP

(57) ABSTRACT

The present invention relates to extracts of *Isochrysis* sp., preferably Tahitian *Isochrysis*, its cosmetic, dermatological and/or therapeutic uses and compositions and cosmetic, dermatological or therapeutic products comprising such an extract of *Isochrysis* sp., preferably Tahitian *Isochrysis*.

6 Claims, 9 Drawing Sheets

(56) References Cited

OTHER PUBLICATIONS

19 Herbal remedies for hair growth. Retrieved from the internet on Mar. 2, 2019. Retrieved from: <URL: https://www.healthline.com/health/herbs-for-hair-growth>. (Year: 2019).*

Grima, Molina E. et al, "Comparison Between Extraction of Lipids and Fatty Acids from Microalgal Biomass," Journal of the American Oil Chemists', vol. 71, No. 9, Sep. 1, 1994, pp. 955-959 XP001118743.

Extended European Search Report, European Application No. 09171485.7, dated Jul. 10, 2012.

Japanese Office Action received in the parallel Japanese Application.

* cited by examiner

EXTRACTS OF ISOCHRYSIS SP.

CROSS-REFERENCE TO RELATED APPLICATION

This application claims benefit of priority to U.S. Provisional Application No. 61/101,228, filed on Sep. 30, 2008, which is incorporated herein by reference in its entirety.

The present invention relates to extracts of *Isochrysis* sp., preferably Tahitian *Isochrysis*, its cosmetic, dermatological and/or therapeutic uses and compositions and cosmetic, dermatological or therapeutic products comprising such an extract of *Isochrysis* sp., preferably Tahitian *Isochrysis*.

In the field of cosmetic and dermatology, there exists a need to provide agents for influencing or modifying the growth of human hair, i.e. to provide agents for increasing the speed of human hair growth and/or for stimulating hair growth from otherwise non-productive hair follicles. Likewise, agents for influencing or modifying growth of human hair that reduce the speed of growth of human hair and/or for unhairing are sought. Preferably, the influencing or modifying of the growth of human hair should be locally confinable.

On the other hand, in the field of cosmetics there are sought agents for influencing or modifying pigmentation of human skin and/or hair, i.e. agents for increasing coloration of human skin and/or hair (hereinafter also called "browning" or "tanning") or for decreasing pigmentation of the skin and/or hair (hereinafter also called "lightening").

Hair growth is not a continuous, steadily ongoing procedure, but instead results from the production of hair material in hair follicles that undergo several stages of a hair growth cycle. During a rest phase of the hair follicle, no significant amount of hair material is produced, while during a hair production phase the production of hair material is started or continued. Some hair follicles turn into an apparently dormant state, in which for an apparently indefinite time no further hair material is produced, resulting in a loss of hairs.

Genetic disposition as well as the natural aging process and/or disease contribute to hair loss and slower hair growth in both males and females. Approximately 50% of the population displays this trait to some degree by the age of 50, where thinning of the hair can begin between 12 and 40 years of age independent of gender (Otberg N et al., Endocrinol Metab Clin North Am. 2007, 36(2), 379-398 and Price V H., Investig Dermatol Symp Proc. 2003, 8 (1), 24-27).

To increase the growth of human hair it has thus been proposed to prolong the phase of production of hair material and/or to shorten the resting phase of hair follicles, e.g. by reactivating apparently dormant hair follicles. Thus, agents able to stimulate hair growth as well as prevent and slow down or reduce hair loss could be beneficial not only as a cure for alopecia but also as positively affect the psychosocial events associated with hair disorders. Studies reveal psychosocial impact with hair loss to include body image dissatisfaction associated with negative stereotypes such as feeling older, weaker and less attractive (S. Pickard-Holley, Sem. Oncol. Nurs. 1995, 11, 235-238).

Various agents for stimulating hair growth have been proposed. Drugs, including Minoxidil (Rogaine), Finasteride (Propecia) and Dutasteride (Avodart) are approved treatments for hair loss. However, they require medical prescription, and are active only on a certain percentage of the population. Moreover, some of these drugs are not permitted to be used by females because of hormonal effects. Thus, premenopausal women should not take Finesteride due to the risk of abnormalities in male fetus when becoming pregnant (S. Krus et al., J. Appl. Cosmetol. 2007, 25, 59-74).

Minoxidil is a drug that is effective in inducing hair growth for a small percentage of patients and will re-grow hair only on top of the scalp. Adverse effects when taken orally are tachycardia, angina pectoris and fluid retention. When applied topically adverse effects are mainly dermatologic, i.e. local irritation, itching, dryness and erythema (S. Krus et al., J. Appl. Cosmetol. 2007, 25, 59-74).

Other medical treatments available to treat hair loss include drastic surgical techniques such as scalp reduction, scalp flaps or follicular unit transplantation. These surgeries carry the risk of complications such as elevation of hairline associated with donor region, possibility of necrosis and unnatural appearance of hair growth direction, anesthesia and post-op care, not to mention high costs.

Herbal preparations that claim to induce hair growth (e.g. Hair Prime) are available at low cost but their effectiveness is often very limited.

On the other hand, it is sometimes desirable to unhair parts of a human body. Thus, it is for example generally preferred to have hair on the scalp but very often hair is unwanted on other parts of the body, especially on the legs, under the arms and on the face. Furthermore there are pathological hair growth disorders (e. g. hirsutism, folliculitis, pseudofolliculitis barbea) that require medical treatment.

Various procedures have been employed to remove unwanted hair, including shaving, electrolysis, depilatory creams or lotions, waxing, plucking, and therapeutic antiandrogens. These conventional procedures generally have drawbacks associated with them. Shaving, for instance, can cause nicks and cuts, and can leave a perception of an increase in the rate of hair regrowth. Shaving also can leave an undesirable stubble. Electrolysis, on the other hand, can keep a treated area free of hair for prolonged periods of time, but can be expensive, painful, and sometimes leaves scarring. Depilatory creams, though very effective, typically are not recommended for frequent use due to their high irritancy potential. Waxing and plucking can cause pain, discomfort, and poor removal of short hair. Finally, antiandrogens, which have been used to treat female hirsutism, can have unwanted side effects.

Skin- or hair-lightening active ingredients intervene in one form or another in melanin metabolism or catabolism. Melanin pigments, which are normally brown to black in colour, are formed in the melanocytes of the skin, transferred to the keratinocytes and give the skin or hair its colour. In mammals, the brown-black eumelanins are primarily formed from hydroxy-substituted aromatic amino acids such as L-tyrosine and L-DOPA, the yellow to red pheomelanins additionally from sulfur-containing molecules (Cosmetics & Toiletries 1996, 111 (5), 43-51). Starting from L-tyrosine, L-3,4-dihydroxyphenylalanine (L-DOPA) is formed by the copper-containing key enzyme tyrosinase and is in turn converted by tyrosinase to dopachrome. By a series of steps catalysed by various enzymes, the latter is oxidised to form melanin.

Skin-lightening agents are used for various reasons: if for some reason the melanin-forming melanocytes in human skin are not evenly distributed, pigment spots occur which are either lighter or darker than the surrounding skin area. To overcome this problem, skin and hair lightening agents are sold which at least partially help to balance out such pigment spots. In addition, many people have a need to lighten their naturally dark skin colour or to prevent skin pigmentation. Hair-lightening agents are useful to lighten regrowing unwanted hair and make it thus less noticeable. In addition, many people have the desire to lighten their naturally dark hair colour. This requires very safe and effective skin and hair lightening agents. Many skin and hair lightening agents contain more or less powerful tyrosinase inhibitors. This is only one possible route towards skin and hair lightening, however.

Furthermore, UV-absorbing substances are also used to protect against the increase in skin pigmentation caused by UV light. This is a purely physically induced effect, however, and must be distinguished from the biological action of skin-lightening agents on cellular melanin formation, which can also be detected in the absence of UV light. Moreover, UV absorbers do not bring about a true lightening of the skin but merely inhibit the increase in skin pigmentation caused by UV light.

Hydroquinone, hydroquinone derivatives such as e.g. arbutin, vitamin C, derivatives of ascorbic acid such as e.g. ascorbyl palmitate, kojic acid and derivatives of kojic acid such as e.g. kojic acid dipalmitate, are used in particular in commercial cosmetic or therapeutic skin and hair lightening formulations.

One of the most commonly used skin and hair lighteners is hydroquinone. However, this compound has a cytotoxic effect on melanocytes and is irritating to the skin. For that reason such preparations are no longer authorised for cosmetic applications in Europe, Japan and South Africa, for example. In addition, hydroquinone is very sensitive to oxidation and can be stabilised only with difficulty in cosmetic formulations. Arbutin is a hydroquinone glucoside, which hydrolyses in situ to form hydroquinone and is therefore just as questionable in toxicological terms as hydroquinone.

Vitamin C and ascorbic acid derivatives have only an inadequate effect on the skin. Furthermore, they do not act directly as tyrosinase inhibitors but instead reduce the coloured intermediate stages of melanin biosynthesis.

Kojic acid (5-hydroxy-2-hydroxymethyl-4-pyranone) is a tyrosinase inhibitor which inhibits its catalytic action by chelating the copper atoms in the enzyme; it is used in commercial skin and hair lightening agents but has a high sensitising potential and causes contact allergies.

On the other hand, it is sometimes desirable to tan parts of the body. Skin and hair browning agents can at least partially help to balance out pigment spots if the melanin-forming melanocytes are not evenly distributed. In addition, many people need to tint their naturally pale skin colour and to develop skin pigmentation without being exposed to solar radiation. In addition, some people have the desire to obtain a more intense and homogeneous hair colour. For this reason very safe and effective skin and hair browning agents are necessary.

It is also known that in fair-skinned people high exposure to the sun can cause the breakdown of the vitally important B vitamin folic acid. Folic acid deficiency in pregnancy for example leads to severe deformities. Folic acid is also necessary for DNA synthesis and is therefore essential for sperm production. Folic acid deficiency can therefore lead to infertility. A protection against UV radiation accordingly prevents folic acid deficiency.

Artificial skin browning can be carried out cosmetically or medically, the following main approaches playing a part:

If carotene preparations are taken regularly, carotene is stored in the fatty tissue of the subcutis and the skin gradually turns orange to yellow-brown.

Washable makeup preparations can be used to achieve a light skin tinting (e.g. extracts of fresh green walnut shells, henna).

Skin browning can also be achieved by chemical changes to the skin's stratum corneum using so-called self-tanning preparations. The most important active ingredient is dihydroxyacetone. The skin browning achieved in this way does not wash off and is only removed with the normal flaking of the skin (after around 5 to 10 days). Dihydroxyacetone can be classed as a ketotriose and as a reducing sugar it reacts with the amino acids in the skin or the free amino and imino groups in keratin via a series of intermediate steps along the lines of a Maillard reaction to form brown-coloured substances known as melanoids, which are occasionally also called melanoidins.

One disadvantage of this is that unlike "sun-tanned" skin, the skin browning obtained with dihydroxyacetone does not protect the skin against sunburn. A further disadvantage of dihydroxyacetone lies in the fact that, particularly under the influence of ultraviolet radiation, it releases formaldehyde, albeit usually in small amounts. Dihydroxyacetone also has an unpleasant, chemical odour.

The tint obtained with self-tanning agents is achieved without exposure to sunlight. In contrast, so-called "pre-tan products" or "tan promoters" are also available, which have to be applied before exposure to sunlight. In the sun these preparations then turn yellow, giving rise to a light brown-yellow colouring of the epidermis which further boosts the "suntan".

Another type of artificial browning which is not dependent on UV light can be brought about through the hormones which are usually also released in the body as a consequence of (natural) UV irradiation and ultimately stimulate the melanocytes to synthesise melanin. Examples which can be cited in this connection are derivatives of proopiomelanocortin (POMC) such as [alpha]-MSH (Melanocyte Stimulating Hormone) and synthetic variants (such as [Nle(4), D-Phe(7)]-[alpha]-MSH), which in some cases display far higher activity levels than the natural [alpha]-MSH. Although these hormones can cause browning in principle, their use in cosmetics is prohibited, since they are pharmacologically potent substances (hormones) which should not be widely used without medical indications. There exists thus in the art an ongoing need to provide further agents for influencing or modifying growth of human hair and/or pigmentation of human skin and/or hair.

According to the invention, there is thus provided a method of obtaining a composition for influencing or modifying a) growth of human hair and/or b) pigmentation of human skin and/or hair, comprising the step of extracting cell material of *Isochrysis* sp., preferably Tahitian *Isochrysis*, with a liquid extractant selected from the group consisting of hexane, ethyl acetate, ethanol, water, methanol, isopropanol and mixtures of two or more of these extractants, wherein the extraction comprises a) exposition of the cell material to the extractant for up to 24 h at a temperature of not more than 50° C., and b) removal of the cell material to obtain an extract, the extract being the composition or being further processed into the composition.

Microalgae have been used in the field of cosmetics before. For example, EP 1 745 794 A2 discloses the use of microalgae or microalgae extracts for preventing or treating protozoal infections in human or animals. Also, U.S. Pat. No. 5,767,095 discloses topical anti-inflammatory compositions comprising monogalactosyl-dieicosapentanoyl glycerol obtained from *Isochrysis galbana*. Whole cells of *Isochrysis galbana* have been used in FR 2 801 788 and FR 2 676 454 for achieving a stabilized redox potential and for reconstituting of abiotic sea water for thalassotherapy. Also, several documents like EP 1 886 679, EP 918 517 B1 and WO 94/24984 describe processes for obtaining specific substances by extraction of microalgae cells. None of the documents teaches or suggests the usefulness of *Isochrysis* and particularly of Tahitian *Isochrysis* for influencing or modifying the growth of human hair and/or pigmentation of human skin and/or hair.

US 2006/269497 discloses the use of astaxanthin as a trichogenous agents and also indicates that astaxanthin can be found in microalgae. *Isochrysis* and particularly Tahitian *Isochrysis* is not mentioned.

JP 2002-068943 A generally discloses uses of extracts or several microalgae species and genera for inhibiting testosterone-5-alpha-reductase. The order *Isochrysis* is generally mentioned. However, the document also mentions that special culturing is necessary for obtaining microalgae cells, and different cultural conditions are required for each microalgae species. The document does not disclose culturing conditions for genus *Isochrysis*.

FR 2657012 A1 discloses in example 8 an extract of *Isochrysis* algae obtained by introducing the algae in aqueous ethanol (water:ethanol=19:1 (v/v)) and disintegrating said algae with a mixer having high shear forces (Ultra Turrax). After disintegration, extraction was carried out for 24 hours at 20° C. The disrupted algae were subsequently separated off by filtration. In contrast to this, in the context of the present invention the microalgae are not disintegrated before extraction. Instead, the cell material is substantially or completely intact or freeze-dried. Extracts obtained or obtainable from disrupted *Isochrysis* algae clearly differ from those obtained in accordance with the present invention. According to the present invention cell material is considered substantially or completely intact if the cell membrane of 90% of cells of a sample comprising 100 or more cells is intact, preferably as determined by propidium iodide staining and optical inspection.

Thus, in the context of the present invention the "cell material of *Isochrysis* sp." and particularly "cell material of Tahitian *Isochrysis*" refers to a composition of freeze-dried, substantially or completely intact cells or mixtures thereof, wherein the cells are *Isochrysis* sp. cells or Tahitian *Isochrysis* cells, respectively. The cell material can comprise a carrier medium, provided that the total content of disrupted cells is less than 10% of all cells, preferably as determined as propidium iodide staining. In summary, what is extracted according to the present invention is not a homogenized or substantially disrupted mass of cells. Instead, the cell material according to the present invention is preferably obtained by a method consisting of the following steps:

1. Cultivating *Isochrysis* sp. cells and/or preferably of Tahitian *Isochrysis* cells,
2. Harvesting the cells to obtain completely or substantially intact cell material,
3. Optionally washing the cell material of step 2 once or multiple times, to obtain washed, substantially or completely intact cell material,
4. Optionally freeze-drying the cell material of step 2 and/or step 3.

It is generally known that different biological species comprise different substances. Thus, effects obtainable by use of one microalgae species cannot be used to predict the effects obtainable by use of a different microalgal species. Furthermore, as will be shown hereinafter, the effects obtainable by extracts of *Isochrysis* sp., preferably Tahitian *Isochrysis*, largely depend on the exact extraction conditions and may even be reversed upon modification of the extraction method used.

It was thus surprising that extracts of *Isochrysis* sp., preferably Tahitian *Isochrysis*, are useful for influencing or modifying growth of human hair and/or pigmentation of human skin and/or hair. Also, the extracts of the present invention favourably allow the production of effective compositions by simple and reliable methods starting from biological materials, i.e. microalgal cell material.

*Isochrysis* sp., preferably Tahitian *Isochrysis*, is employed for obtaining extracts and compositions according to the present invention. Tahitian *Isochrysis* is a strain of *Isochrysis* collectable at Mataiva (Tahiti). According to the present invention, strain CS 177 obtainable from the Australian CSIRO collection (also registered as CCMP1324 at Provasoli-Guillard National Center for Culture of Marine; NEPCC601 at the Canadian Center for the Culture of Microorganisms) is preferably used. This strain has been isolated by K. Haines in 1977 at Mataiva, Tahiti.

According to the present invention, cell material of *Isochrysis* sp., preferably Tahitian *Isochrysis*, is extracted with a liquid extractant selected from the group consisting of hexane, ethyl acetate, ethanol, water, methanol. The extractant can also be a mixture of two or more of the aforementioned extractants such as for example a mixture of hexane/ ethyl acetate 1:1 (v/v). These extractants have provided best results for influencing or modifying growth of human hair and/or pigmentation of human skin and/or hair.

For extraction, the cell material is in step a) contacted with the liquid extractant for up to 24 h at a temperature of not more than 50° C., preferably at a temperature of 16-40° C. and most preferably at a temperature of 20-30° C. Also, exposition of the cell material to the extractant preferably lasts for up to 24 h, more preferably for 1-10 h and most preferably for 2-6 h. For all extraction conditions described herein, best results have been achieved when the extraction was performed in the dark. Also, during contact of the cell material with the extractant the material is preferably agitated, preferably by stirring.

Preferably, the ratio (w:v) of cell material to liquid extractant is 200 mg:1 ml to 1 mg:1 ml, more preferably 140 mg:1 ml to 5 mg:1 ml, and most preferably 80 mg:1 ml to 10 mg:1 ml when using freeze-dried cell material as detailed below.

After extraction, in step b) an extract is obtained by removal of the cell material, preferably by centrifugation, filtration or decantation or other suitable methods. A particle-free supernatant according to visual inspection is thus obtained, typically of yellow-greenish to brown-greenish colour. The extract can be used as a composition for influencing or modifying growth of human hair and/or pigmentation of human skin and/or hair, or, more preferably, is further processed into such composition as detailed below.

The cell material removed from the extract in step b) can be used for another exposition to the extractant in step a), typically for a few minutes, preferably up to 1 h. The extraction thus preferably comprises repeating steps a) and b) once, twice, three or four times, preferably once or twice, and in each step a) the cell material removed in the respective prior step b) is used, and the extracts of steps b) are combined. This way, a continued extract with reproducible composition and high yield of extracted active ingredients can be obtained.

In a preferred method according to the present invention, the cell material used in a step a) of the extraction is obtained in step b) of a prior extraction with a different extractant. Thus, two extracts or compositions are provided, and the method can be repeated to provide further extracts or compositions.

Particularly preferred are extracts and compositions obtainable or obtained by the following extractions:
1. Extraction with ethyl acetate, followed by extraction with ethanol, followed by extraction with water or extraction with ethyl acetate followed by extraction with 30% aqueous ethanol or with water
2. Extraction with methanol or ethanol, followed by extraction with water
3. Extraction with hexane, followed by extraction with ethyl acetate, followed by extraction with ethanol, followed by extraction with water.
4. Extraction with methanol or ethanol, followed by extraction with a mixture of hexane/ethyl acetate 1:1 (v/v), hexane or ethyl acetate followed by extraction with water The phototoxicity of the extracts and composition is preferably adjusted to a phototoxicity index of less than 5 according to the Official Journal of the European Communities, directive 2000/33/EG of the commission from 25 Apr. 2000, appendix II, B.41 and the OECD Guideline 432. At a phototoxicity index of less than 5, the composition is no longer considered to possess phototoxic potential.

For adjusting phototoxicity the optionally combined extract—not in solid form—is preferably treated with activated carbon in a ratio dry extract:activated carbon of 3:1 to 1:20 (w/w), preferably 1:1 to 1:12 (w/w). The term 'dry extract' according to the present invention refers to the extractant-free weight of an extract according to the present invention, e.g. as obtainable by completely removing the extractant. This treatment may result in a minor loss of activity for influencing or modifying the growth of human hair and/or pigmentation of human skin and/or hair. However, the treatment reliably removes phototoxic ingredients otherwise comprised in the extract. A further benefit of this treatment is a colour reduction of most of the extracts.

For preparing the composition, the extractant is preferably removed from the—optionally combined—extract, preferably by evaporation or other suitable processes, to obtain the extract in concentrated or dry form (dry extract), the latter preferably as a suspension, a viscous liquid, a powder or as granules. The concentrated form preferably contains 50-80 wt. % dry matter and 50-20 wt. % residual extractant.

The composition is then formed by optionally adding a cosmetically and/or dermatologically and/or therapeutically acceptable solid carrier to the extract in concentrated or dry form (dry extract) and then optionally drying the mixture by suitable processes. In this context, such a solid which is at least not toxic to the organisms on which it is to be used is cosmetically, dermatologically or therapeutically acceptable. Preferred solids are hydrocolloids such as starches, degraded or chemically or physically modified starches (in particular dextrins and maltodextrin), lactose, modified celluloses, gum arabic, gum ghatti, tragacanth gum, karaya, carrageenan, pullulan, curdlan, xanthan gum, gellan gum, guar gum, locust bean gum, alginates, agar, pectin, inulin or glucose and mixtures of two or more of these solids.

The composition can also be formed by optionally adding a cosmetically and/or dermatologically and/or therapeutically acceptable solvent, such as e.g. neutral oil, mineral oil, silicone oil, plant oils, triglycerides, fatty alcohols, fatty acid esters, polyol fatty acid esters such as PEG-7 glyceryl cocoate available e.g. as Cetiol HE from Cognis, ethanol, 1,2-propylene glycol, 1,3-butylene glycol, dipropyleneglycol, triethyl citrate, 1,2-pentanediol or other 1,2-alkanediols, glycerin and water and mixtures of two or more of these solvents to the extract in concentrated or dry form (dry extract) and optionally completely removing the residual extractant by a suitable process. Such compositions prepared according to the invention are readily further processable in particular for cosmetic purposes. These compositions can optionally be prepared with the addition of a solubilizing agent, preservative or antioxidant.

Most preferably, 1,2-pentanediol or 1,2-hexanediol or a mixture of one of these diols and one or more of the above mentioned solvents for example a mixture of water and 1,2-diol is selected as solvent. The diols not only possess very good solubilizing properties but exhibit also bioavailability enhancing and moisturizing activity. Furthermore, depending on the concentration of the 1,2-diol no further preservation or only reduced levels of preservatives are needed to protect the composition from microbial growth. Antioxidants such as for example tocopherol or tocopherol mixtures, tocopherol acetate, BHT or other suitable antioxidants are also easily incorporated.

For very lipophilic extracts such as for example hexane or ethyl acetate extracts, neutral oil, mineral oil, silicone oil, plant oils, triglycerides, fatty alcohols, fatty acid esters, polyol fatty acid esters, dipropylenglycol, triethyl citrate and ethanol and mixtures of two or more of these solvents are prefered.

The extract or the liquid or solid composition comprising the extract can furthermore also be further processed by encapsulation with a solid shell material, which is preferably chosen from starches, degraded or chemically or physically modified starches (in particular dextrins and maltodextrins), gelatines, wax materials, liposomes, gum arabic, agar-agar, ghatti gum, gellan gum, modified and non-modified celluloses, pullulan, curdlan, carrageenans, algic acid, alginates, pectin, inulin, xanthan gum and mixtures of two or more of the substances mentioned.

The solid shell material is preferably selected from gelatine (pork, beef, poultry and/or fish gelatines and mixtures thereof are advantageous, preferably including at least one gelatine having a Bloom value of greater than or equal to 200, preferably having a Bloom value of greater than or equal to 240), maltodextrin (preferably obtained from maize, wheat, tapioca or potato, preferred maltodextrins displaying a DE value in the range from 10 to 20), modified cellulose (e.g. cellulose ether), alginates (e.g. Na alginate), carrageenan (beta-, iota-, lambda- and/or kappa-carrageenan), gum arabic, curdlan and/or agar-agar. Gelatine is used in particular because of its good availability in various Bloom values. Production can take place as described for example in EP 0 389 700 A, JP 7 196 478, U.S. Pat. No. 4,251,195, 6,214,376, WO 03/055587 or WO 2004/050069.

The compositions in liquid, solid (other than the dry extract) or encapsulated form obtainable or obtained according to the present invention comprise 0.001 to 20 wt. %, preferably 0.01 to 10 wt % and most preferably 0.1-5 wt % dry extract relative to the total composition.

According to the invention, a composition for stimulating growth of human hair without or with only low activity in influencing pigmentation of human skin and/or hair is provided, the composition being or comprising an extract obtained by using methanol as extractant. It has surprisingly been found that by directly extracting *Isochrysis* sp., preferably Tahitian *Isochrysis*, cell material, particularly freeze-dried material, with methanol, the aforementioned effects can be achieved.

Further according to the invention, a composition for stimulating growth of human hair and increasing pigmentation of human skin and/or hair is provided, wherein the composition is or comprises an extract obtained by using ethyl acetate as extractant. It has surprisingly been found that by directly extracting *Isochrysis* sp., preferably Tahitian *Isochrysis*, cell material, particularly freeze-dried material, with ethyl acetate, the aforementioned effects can be achieved.

Furthermore according to the invention, a composition for stimulating growth of human hair and increasing pigmentation of human skin and/or hair is provided, wherein the composition is or comprises an extract obtained by using a hexane/ethyl acetate 1:1 (v/v) mixture after first extracting the biomass with methanol as extractant. It has surprisingly been found that by extracting *Isochrysis* sp., preferably Tahitian *Isochrysis*, cell material, particularly freeze-dried material, with methanol followed by extraction with hexane/ethyl acetate 1:1 (v/v), the aforementioned effects can be achieved. A further benefit of this extract is the very light yellowish colour. Also according to the invention, a composition for increasing pigmentation of human skin and/or hair without or with only low activity in stimulating growth of human hair, wherein the composition is or comprises an extract obtained by using water as extractant. It has surprisingly been found that by extracting *Isochrysis* sp., preferably Tahitian *Isochrysis*, cell material with water, preferably after prior extraction of freeze-dried material with methanol, ethanol, ethyl acetate and/or hexane or mixtures of two or more of these solvents, the aforementioned effects can be achieved.

For inhibiting growth of human hair while increasing pigmentation of human skin and/or hair, a composition is provided according to the invention that is or comprises an extract obtained by using ethanol as extractant on cell material obtained after extraction with ethylacetate or with hexane followed by extraction with ethylacetate. Again surprisingly, such composition allows to achieve the aforementioned effects.

Also according to the invention there is provided a composition for inhibiting growth of human hair and decreasing pigmentation of human skin and/or hair, wherein the composition is or comprises an extract obtained by using ethanol as extractant. It has surprisingly been found that by directly extracting *Isochrysis* sp., preferably Tahitian *Isochrysis*, cell material, particularly freeze-dried material, with ethanol, the aforementioned effects can be achieved.

The composition of the present invention can favourably be part of a cosmetic, dermatologic or therapeutic product. In such product the composition is preferably present in an amount sufficient to achieve the aforementioned effects upon application of the product to the human skin and/or hair or after oral consumption.

The concentration of the composition in a cosmetic, dermatological or therapeutic product (for topical or oral application) preferably is
  at least 0.001 ppm, preferably at least and 0.01 ppm and most preferably at least 0.1 ppm, and
  at most 100 ppm, preferably at most 50 ppm and most preferably at most 10 ppm
dry extract of the total product.

The cosmetic, dermatological or therapeutic products according to the invention are produced by conventional processes known per se, such that the extract or the extract composition is incorporated into cosmetic, dermatological or therapeutic products which can have a conventional composition and which in addition to the aforementioned effects can also be used for the treatment, care and cleansing of the skin or hair.

Essential fields of use for extract or extract compositions according to the invention are cosmetic, dermatological or therapeutic products which (apart from the presence of the extract according to the invention) serve for cosmetic or dermatological light protection, for treatment, care and cleansing of the skin and/or hair or as a make-up product in decorative cosmetics. Such products can accordingly be present e.g. as a cleansing composition, such as e.g. soap, syndet, liquid washing, shower and bath preparation, skin care composition, such as e.g. emulsion (as a solution, dispersion, suspension; cream, lotion or milk of the W/O, O/W or multiple emulsion, PIT emulsion, emulsion foam, micro- or nanoemulsion, Pickering emulsion type, depending on the preparation process and constituents), ointment, paste, gel (including hydro-, hydrodispersion-, oleogel), alcoholic or aqueous/alcoholic solution, oil, toner, balsam, serum, powder (e.g. face powder, body powder), soaking liquid for wipes, Eau de Toilette, Eau de Cologne, perfume, wax, including the presentation form as a mask, mousse, stick, pencil, roll-on, (pump) spray, aerosol (foaming, non-foaming or after-foaming), skin care composition (as described above) as a foot care composition (including keratolytics, deodorant), as an insect repellent composition, as a sunscreen composition, as a self-tanning composition and/or aftersun preparation, skin care composition as a shaving composition or after-shave, as a hair-removing composition, as a hair care composition, such as e.g. shampoo (including shampoo for normal hair, for greasy hair, for dry, stressed (damaged) hair, 2-in-1 shampoo, anti-dandruff shampoo, baby shampoo, shampoo for a dry scalp, shampoo concentrate), conditioner, hair treatment cure, hair tonic, hair lotion, hair rinse, styling cream, pomade, permanent wave and fixing compositions, hair smoothing composition (straightening composition, relaxer), hair setting composition, styling aid (e.g. gel or wax); blonding composition, hair colouring composition, such as e.g. temporary, directly absorbed, semi-permanent hair colouring composition, permanent hair colouring composition), skin care composition as a decorative body care composition, such as e.g. nail care composition (nail varnish and nail varnish remover), decorative cosmetic (e.g. powder, eye shadow, kajal pencil, lipstick, mascara), make-up, make-up remover, skin care composition as a deodorant and/or antiperspirant.

It is also advantageous to administer the extract or extract composition orally e.g. in the form of tablets, dragees, capsules, juices, solutions and granules or in form of orally consumable products used for alimentation which in addition to their function as foodstuff provide beauty from inside.

Compositions according to the present invention can advantageously be combined, in particular in cosmetic products, with further conventional components, such as, for example:
  preservatives, in particular those described in US 2006/0089413, antimicrobial agents, such as e.g. antibacterial agents or agents to treat yeast and mold, in particular those described in WO 2005/123101, antiacne and sebum reducing agents, in particular those described in WO 2008/046791, compounds against ageing of the skin, in particular those described in WO 2005/123101, antidandruff agents, in particular those described in WO 2008/046795, antiirritants (antiinflammatory agents, irritation-preventing agents, irritation-inhibiting agents), in particular those described in WO 2007/042472 and US 2006/0089413, antioxidants, in particular those described in WO 2005/123101, carrier materials, in particular those described in WO 2005/123101, chelating agents, in particular those described in WO 2005/123101, deodorizing agents and antiperspirants, in particular those described in WO 2005/123101, moisture regulators (moisture-donating agents, moisturizing substance, moisture-retaining substances), in particular those described in WO 2005/123101, osmolytes, in particular those described in WO 2005/123101, compatible solutes, in particular those described in WO 01/76572 and WO 02/15868, proteins and protein hydrolysates, in particular those described in WO 2005/123101 and WO2008046676, skin-lightening agents, in particular those described in WO 2007/110415, skin-tanning agents, in particular those described in WO 2006/045760, cooling agents, in particular those described in WO 2005/123101, skin-cooling agents, in particular those described in WO 2005/123101, warming agents, in particular those described in WO 2005/123101, UV-absorbing agents, in particular those described in WO 2005/123101, UV filters, in particular those described in WO 2005/123101, benzylidene-beta-dicarbonyl compounds in accordance with WO 2005/107692 and alpha-benzoyl-cinnamic acid nitriles in accordance with WO 2006/015954, insect repellents, in particular those described in WO 2005/123101, plant parts, plant extracts, in particular those described in WO 2005/123101, vitamins, in particular those described in WO 2005/123101, emulsifiers, in particular those described in WO 2005/123101, gelling agents, in particular those described in WO 2005/123101, oils in particular those described in WO 2005/123101, waxes in particular those described in WO 2005/123101, fats in particular those described in WO 2005/123101, phospholipids, in particular those described in WO 2005/123101, saturated fatty acids and mono- or poly-unsaturated fatty acids and α-hydroxy acids and polyhydroxy-fatty acids and esters of saturated and/or unsaturated branched and/or unbranched alkane carboxylic acids, in particular those described in WO 2005/123101, surface-active substances (surfactants) in particular those described in WO 2005/123101, skin repair agents comprising cholesterol and/or fatty acids and/or ceramides and/or pseudoceramides, in particular those described in WO 2006/053912, dyestuffs and colorants and pigments, in particular those described in WO 2005/123101, aroma chemicals and flavors and fragrances, in particular those described in S. Arctander, Perfume and Flavor Chemicals, private publishing house, Montclair, N.J., 1969 and Surburg, Panten, Common Fragrance and Flavor Materials, 5th Edition, Wiley-VCH, Weinheim 2006, preferably those explicitly mentioned in US 2008/0070825, alcohols and polyols, in particular those described in WO 2005/123101, organic solvents, in particular those described in WO 2005/123101, silicones and silicone oils and silicone derivatives in particular those described in WO2008046676, virucides, abrasives, anticellulite agents, astringents, antiseptic agents, antistatics, binders, buffers, cell stimulants, cleansing agents, care agents, depilatory agents, softeners, enzymes, essential oils, in particular those described in US 2008/0070825, fibres, film-forming agents, fixatives, foam-forming agents, foam stabilizers, substances for preventing foaming, foam boosters, gel-forming agents, hair growth activators, hair growth inhibitors, hair care agents, hair-setting agents, hair-straightening agents, hair-smoothening, bleaching agents, strengthening agents, stain-removing agents, optically brightening agents, impregnating agents, dirt-repellent agents, friction-reducing agents, lubricants, opacifying agents, plasticizing agents, covering agents, polish, gloss agents, polymers in particular those described in WO2008046676, powders, peptides, mono-, di- and oligosaccharides, re-oiling agents, abrading agents, skin-soothing agents, skin-cleansing agents, skin care agents, skin-healing agents, skin-protecting agents, skin-softening agents, skin-smoothing agents, nourishing agents, skin-warming agents, stabilizers, detergents, fabric conditioning agents, suspending agents, thickeners, yeast extracts, algae or microalgae extracts, animal extracts, liquefiers, color-protecting agents, anti-corrosives and electrolytes.

Auxiliary substances and additives can be included in quantities of 5 to 99.99 wt. %, preferably 10 to 80 wt. %, based on the total weight of the product. The amounts of cosmetic or dermatological auxiliary agents and additives and perfume to be used in each case can easily be determined by the person skilled in the art by simple trial and error, depending on the nature of the particular product.

The products can also contain water in a quantity of up to 99.99 wt. %, preferably 5 to 80 wt. %, based on the total weight of the product.

Products according to the invention can contain one or more further hair growth modulating agents. A more rapid hair growth modulation based in part on synergistic effects can be achieved in this way.

Agents to stimulate hair growth are for example pyrimidine derivatives such as 2,4-diaminopyrimidine-3-oxide (Aminexil), 2,4-diamino-6-piperidinopyrimidine-3-oxide (Minoxidil) and derivatives thereof, 6-amino-1,2-dihydro-1-hydroxy-2-imino-4-piperidinopyrimidine and its derivatives, pyridoxine hydrochloride, xanthine alkaloids such as caffeine, theobromine and theophylline and derivatives thereof, 6-(benzylamino)purin also known as cytokinin B, pantotenic acid and its derivatives, quercetin and derivatives, dihydroquercetin (taxifolin) and derivatives, potassium channel openers, antiandrogenic agents, synthetic or natural 5-reductase inhibitors, nicotinic acid esters such as tocopheryl nicotinate, benzyl nicotinate and C1-C6 alkyl nicotinate, proteins such as for example the tripeptide Lys-Pro-Val, diphencypren, hormons, finasteride, dutasteride, flutamide, bicalutamide, pregnane derivatives, progesterone and its derivatives, cyproterone acetate, spironolactone and other diuretics, calcineurin inhibitors such as FK506 (Tacrolimus, Fujimycin) and its derivatives, Cyclosporin A and derivatives thereof, glyceryl monopentadecanoate or other promoters of ATP production in hair follicles, mononitro guaiacol, biotin, carpronium chloride, tocopherol and its derivatives, cepharanthine, sulphur, vitamin B6, glycyrrhetinic acid and its derivatives, inositol, hinokitiol, methionine, serine, threonine, zinc and zinc salts, polyphenols, procyanidins, proanthocyanidins, phytosterols such as for example beta-sitosterol, biotin, eugenol, (±)-beta-citronellol, panthenol, glycogen for example from mussels, kankohso, placental extract, royal yelly extract, Duku extract, extracts from microorganisms, algae, microalgae or plants and plant parts of for example the genera dandelion (*Leontodon* or *Taraxacum*), *Orthosiphon*, *Vitex*, *Coffea*, *Paullinia*, *Theobroma*, *Asiasarum*, *Cucurbita*, *Swertia*, *Capsicum* or *Styphnolobium*, *Serenoa repens* (saw palmetto), *Sophora flavescens*, *Pygeum africanum*, *Panicum miliaceum*, *Cimicifuga racemosa*, *Glycine max*, *Eugenia caryophyllata*, *Excrementum bombycis*, *Cotinus coggygria*, *Hibiscus rosa-sinensis*, *Camellia sinensis*, *Ilex paraguariensis*, *Polygonum multiflorum*, licorice, grape, ginseng, ginkgo, apple, barley or hops or/nd hydrolysates from rice or wheat.

Agents to inhibit hair growth are for example activin, activin derivatives or activin agonists, ornithine decarboxylase inhibitors such as alpha-difluoromethylornithine or pentacyclic triterpenes like for example ursolic acid, betulin, betulinic acid, oleanolic acid and derivatives thereof, ornithine amino transferase inhibitors, serine proteases, 5alpha-reductase inhibitors, 5-lipoxygenase inhibitors, cyclooxygenase inhibitors, protein-tyrosine kinase inhibitors, protein kinase C inhibitors, sulfotransferase inhibitors, nitric oxide synthetase inhibitors, alkaline phosphatase inhibitors, inhibitors of elastase-like enzymes, neutral endopeptidase inhibitors, matrix metalloproteinase inhibitors, inhibitors of a cysteine pathway enzyme, androgen receptor antagonists, S-adenosylmethionine decarboxylase inhibitors, gamma-glutamyl transpeptidase inhibitors, transglutaminase inhibitors, VEGF modulators, compounds which block the glucose transfer across the membranes of the cells of hair follicles such as phloretin, soybean-derived serine protease inhibitors, extracts from microorganisms, algae, microalgae or plants and plant parts of for example the families Leguminosae, Solanaceae, Graminae, Asclepiadaceae or Cucurbitaceae, the genera *Chondrus, Gloiopeltis, Ceramium, Durvillea, Glycine max, Sanguisorba officinalis, Calendula officinalis, Hamamelis virginiana, Arnica montana, Salix alba, Hypericum perforatum* or *Gymnema sylvestre*.

The amount of the aforementioned examples of additional active ingredients for the modulation of hair growth (one or more compounds) in the formulations according to the invention is then preferably 0.00001 to 30 wt. %, preferably 0.0001 to 20 wt. %, particularly preferably 0.001 to 5 wt. %, based on the total weight of the product.

The products according to the invention can preferably also contain other active ingredients which modulate skin and/or hair pigmentation and which are suitable for cosmetic (e.g. dermatological) and/or therapeutic applications. A more rapid modulation of skin and/or hair pigmentation based in part on synergistic effects can be achieved in this way.

Advantageous skin and hair lightening active ingredients in this respect are kojic acid (5-hydroxy-2-hydroxymethyl-4-pyranone), kojic acid derivatives e.g. kojic acid dipalmitate, arbutin, ascorbic acid, ascorbic acid derivatives, hydroquinone, hydroquinone derivatives, resorcinol, sulfur-containing molecules such as e.g. glutathione or cysteine, alpha-hydroxy acids (e.g. citric acid, lactic acid, malic acid) and derivatives thereof, N-acetyl tyrosine and derivatives, undecenoyl phenylalanine, gluconic acid, 4-alkyl resorcinols, 4-(1-phenylethyl)-1,3-dihydroxybenzene, chromone derivatives such as aloesin, flavonoids, thymol derivatives, 1-aminoethyl phosphinic acid, thiourea derivatives, ellagic acid, nicotinamide (niacinamide), zinc salts such as e.g. zinc chloride or gluconate, thujaplicin and derivatives, triterpenes such as maslinic acid, sterols such as ergosterol, benzofuranones such as senkyunolide, vinyl and ethyl guiacol, dionic acids such as octodecene dionic acid and azelaic acid, inhibitors of nitrogen oxide synthesis, such as e.g. L-nitroarginine and derivatives thereof, 2,7-dinitroindazole or thiocitrulline, metal chelators (e.g. alpha-hydroxy fatty acids, palmitic acid, phytic acid, lactoferrin, humic acid, bile acid, bile extracts, bilirubin, biliverdin, EDTA, EGTA and derivatives thereof), retinoids, soya milk and extract, serine protease inhibitors or lipoic acid or other synthetic or natural active ingredients for skin and hair lightening, the latter also being used in the form of an extract from plants, such as e.g. bear-berry extract, rice extract, papaya extract, liquorice root extract or constituents concentrated therefrom, such as glabridin or licochalcone A, artocarpus extract, extract of *rumex* and *ramulus* species, extracts of pine species (*pinus*) and extracts of *vitis* species or stilbene derivatives concentrated therefrom, extract of saxifrage, mulberry, scutelleria or/and grapes.

Advantageous skin and hair tanning active ingredients in this respect are substrates or substrate analogues of tyrosinase such as L-tyrosine, N-acetyl tyrosine, L-DOPA or L-dihydroxyphenylalanine, xanthine alkaloids such as caffeine, theobromine and theophylline and derivatives thereof, proopiomelanocortin peptides such as ACTH, alpha-MSH, peptide analogues thereof and other substances which bind to the melanocortin receptor, peptides such as Val-Gly-Val-Ala-Pro-Gly, Lys-Ile-Gly-Arg-Lys or Leu-Ile-Gly-Lys, purines, pyrimidines, folic acid, copper salts such as copper gluconate, chloride or pyrrolidonate, 1,3,4-oxadiazole-2-thiols such as 5-pyrazin-2-yl-1,3,4-oxadiazole-2-thiol, curcumin, zinc diglycinate (Zn(Gly)2), manganese(II) bicarbonate complexes ("pseudocatalases") as described for example in EP 0 584 178, tetrasubstituted cyclohexene derivatives as described for example in WO 2005/032501, isoprenoids as described in WO 2005/102252 and in WO 2006/010661, melanin derivatives such as Melasyn-100 and MelanZe, diacyl glycerols, aliphatic or cyclic diols, psoralens, prostaglandins and analogues thereof, activators of adenylate cyclase and compounds which activate the transfer of melanosomes to keratinocytes such as serine proteases or agonists of the PAR-2 receptor, extracts of plants and plant parts of the *chrysanthemum* species, *sanguisorba* species, walnut extracts, urucum extracts, rhubarb extracts, trehalose, erythrulose and dihydroxyacetone. Flavonoids which bring about skin and hair tinting or browning (e.g. quercetin, rhamnetin, kaempferol, fisetin, genistein, daidzein, chrysin and apigenin, epicatechin, diosmin and diosmetin, morin, quercitrin, naringenin, hesperidin, phloridzin and phloretin) can also be used.

The amount of the aforementioned examples of additional active ingredients for the modulation of skin and hair pigmentation (one or more compounds) in the products according to the invention is then preferably 0.00001 to 30 wt. %, preferably 0.0001 to 20 wt. %, particularly preferably 0.001 to 5 wt. %, based on the total weight of the preparation.

Products according to the present invention in the form of cosmetic and/or dermatologically active products are applied to the skin and/or hair in a sufficient amount in the conventional manner for cosmetics and dermatics. In this context, cosmetic and dermatological products according to the present invention which additionally act as sunscreen products offer particular advantages. These products (formulations) advantageously comprise at least one UVA filter and/or at least one UVB filter and/or at least one inorganic pigment. In this context, the products can be in various forms such as are conventionally employed e.g. for sunscreen formulations. They can be e.g. a solution, an emulsion of the water-in-oil (W/O) type or of the oil-in-water (O/W) type or a multiple emulsion, for example of the water-in-oil-in-water (W/O/W) type, a gel, a hydrodispersion, a solid stick or also an aerosol.

As mentioned, products according to the present invention can advantageously be combined with substances which absorb UV radiation, the total amount of the filter substances being e.g. 0.01 to 40 wt.-%, preferably 0.1 to 10 wt.-%, in particular 1.0 to 5.0 wt.-%, based on the total weight of the formulations, in order to provide cosmetic products which protect the hair or skin from ultraviolet radiation.

Preferred products of the present invention are sunscreen formulations in the form of aqueous emulsions, preferably of the water-in-oil (W/O) or of the oil-in-water (O/W) type or a multiple emulsion, for example of the water-in-oil-in-water (W/O/W) type, more preferably of the oil-in-water (O/W) type.

Preferred sunscreen formulations (products) of the present invention comprise a total amount of organic UV filters of greater than 10 wt.-%, preferably in the range of from 12 to 40 wt.-%, more preferred in the range of from 15 to 35 wt.-%, based on the total weight of the sunscreen formulation.

In this context advantageous organic UV filters are:
p-aminobenzoic acid
p-aminobenzoic acid ethyl ester (25 mol) ethoxylated
p-dimethylaminobenzoic acid-2-ethylhexyl ester
p-aminobenzoic acid ethyl ester (2 mol) N-propoxylated
p-aminobenzoic acid glycerol ester
salicylic acid homomenthyl ester (homosalates) (Neo Heliopan®HMS)
salicylic acid-2-ethylhexyl ester (Neo Heliopan®OS)
triethanolamine salicylate
4-isopropyl benzyl salicylate
anthranilic acid menthyl ester (Neo Heliopan®MA)
diisopropyl cinnamic acid ethyl ester
p-methoxycinnamic acid-2-ethylhexyl ester (Neo Heliopan®AV)
diisopropyl cinnamic acid methyl ester
p-methoxycinnamic acid isoamyl ester (Neo Heliopan®E 1000)
p-methoxycinnamic acid diethanolamine salt
p-methoxycinnamic acid isopropyl ester
2-ethylhexyl-2-cyano-3,3-diphenyl acrylate (Neo Heliopan®303)
ethyl-2-cyano-3,3'-diphenyl acrylate
2-phenylbenzimidazole sulfonic acid and salts (Neo Heliopan®Hydro)
3-(4'-trimethylammonium)benzylidene bornan-2-one methyl sulfate
terephthalylidene dibornane sulfonic acid and salts (Mexoryl®SX)
4-t-butyl-4'-methoxydibenzoyl methane (avobenzone)/(Neo Heliopan®357)
β-imidazole-4(5)-acrylic acid (urocanic acid)
2-hydroxy-4-methoxybenzophenone (Neo Heliopan®BB)
2-hydroxy-4-methoxybenzophenone-5-sulfonic acid
dihydroxy-4-methoxybenzophenone
2,4-dihydroxybenzophenone
tetrahydroxybenzophenone
2,2'-dihydroxy-4,4'-dimethoxybenzophenone
2-hydroxy-4-n-octoxybenzophenone
2-hydroxy-4-methoxy-4'-methyl benzophenone
3-(4'-sulfo)benzylidene bornan-2-one and salts
3-(4'-methyl benzylidene)-d,l-camphor (Neo Heliopan®MBC)
3-benzylidene-d,l-camphor
4-isopropyl dibenzoyl methane
2,4,6-trianilino-(p-carbo-2'-ethylhexyl-1'-oxy)-1,3,5-triazine
phenylene bis-benzimidazyl tetrasulfonic acid disodium salt (Neo Heliopan®AP)
2,2'-(1,4-phenylene)-bis-(1H-benzimidazole-4,6-disulfonic acid), mono-sodium salt
N-[(2 and 4)-[2-(oxoborn-3-ylidene)methyl]benzyl]acrylamide polymer
phenol, -(2H-benzotriazol-2-yl)-4-methyl-6-(2-methyl-3(1, 3,3,3-tetramethyl-1-(trimethylsilyl)oxy)disiloxyanyl)propyl), (Mexoryl®XL)
4,4'-[(6-[4-(1,1-dimethyl)aminocarbonyl)phenylamino]-1,3, 5-triazine-2,4-diyl)diimino]-bis-(benzoic acid-2-ethylhexyl ester) (Uvasorb®HEB)
2,2'-methylene bis-(6-(2H-benzotriazol-2-yl)-4-1,1,3,3-tetramethylbutyl)phenol), (Tinosorb®M)
2,4-bis-[4-(2-ethylhexyloxy)-2-hydroxyphenyl]-1,3,5-triazine
benzylidene malonate polysiloxane (Parsol®SLX)
glyceryl ethylhexanoate dimethoxycinnamate
disodium-2,2'-dihydroxy-4,4'-dimethoxy-5,5'-disulfobenzophenone
dipropylene glycol salicylate
sodium hydroxymethoxybenzophenone sulfonate
4,4',4-(1,3,5-triazine-2,4,6-triyltriimino)-tris-benzoic acid tris(2-ethylhexyl ester) (Uvinu®T150)
2,4-bis-[{(4-(2-ethylhexyloxy)-2-hydroxy}phenyl]-6-(4-methoxyphenyl)-1,3,5-triazine (Tinosorb®S)
2,4-bis-[{(4-(3-sulfonato)-2-hydroxypropyloxy)-2-hydroxy}phenyl]-6-(4-methoxyphenyl)-1,3,5-triazine sodium salt
2,4-bis-[{(3-(2-propyloxy)-2-hydroxypropyloxy)-2-hydroxy}phenyl]-6-(4-methoxyphenyl)-1,3,5-triazine
2,4-bis-[{4-(2-ethylhexyloxy)-2-hydroxy}phenyl]-6-[4-(2-methoxyethylcarbonyl)phenylamino]-1,3,5-triazine
2,4-bis-[{4-(3-(2-propyloxy)-2-hydroxypropyloxy)-2-hydroxy}phenyl]-6-[4-(2-ethylcarboxyl)phenylamino]-1, 3,5-triazine
2,4-bis-[{4-(2-ethylhexyloxy)-2-hydroxy}phenyl]-6-(1-methylpyrrol-2-yl)-1,3,5-triazine
2,4-bis-[{4-tris-(trimethylsiloxysilylpropyloxy)-2-hydroxy}phenyl]-6-(4-methoxyphenyl)-1,3,5-triazine
2,4-bis-[{4-(2"-methylpropenyloxy)-2-hydroxy}phenyl]-6-(4-methoxyphenyl)-1,3,5-triazine
2,4-bis-[{4-(1',1',1',3'5',5',5'-heptamethylsiloxy-2"-methylpropyloxy)-2-hydroxy}phenyl]-6-(4-methoxyphenyl)-1, 3,5-triazine
2-(4-diethylamino-2-hydroxybenzoyl)benzoic acid hexyl ester (Uvinul® A Plus)
indanylidene compounds in accordance with WO 02/38537
Organic UV filters which are particularly preferred in products of the present invention (in particular if they are in the form of a sunscreen formulation), preferably in an amount mentioned (above), are:
p-aminobenzoic acid
3-(4'-trimethylammonium)benzylidene bornan-2-one methyl sulfate
salicylic acid homomenthyl ester (Neo Heliopan®HMS)
2-hydroxy-4-methoxybenzophenone (Neo Heliopan®BB)
2-phenylbenzimidazole sulfonic acid (Neo Heliopan®Hydro)
terephthalylidene dibornane sulfonic acid and salts (Mexoryl®SX)
4-tert-butyl-4'-methoxydibenzoyl methane (Neo Heliopan®357)
3-(4'-sulfo)benzylidene bornan-2-one and salts
2-ethylhexyl-2-cyano-3,3-diphenyl acrylate (Neo Heliopan®303)
N-[(2 and 4)-[2-(oxoborn-3-ylidene)methyl]benzyl]acrylamide polymer
p-methoxycinnamic acid-2-ethylhexyl ester (Neo Heliopan®AV)
p-aminobenzoic acid ethyl ester (25 mol) ethoxylated
p-methoxycinnamic acid isoamyl ester (Neo Heliopan®E1000)
2,4,6-trianilino-(p-carbo-2'-ethylhexyl-1'-oxy)-1,3,5-triazine (Uvinul®T150)

phenol, 2-(2H-benzotriazol-2-yl)-4-methyl-6-(2-methyl-3 (1,3,3,3-tetramethyl-1-(trimethylsilypoxy)disiloxyanyl) propyl), (Mexoryl®XL)

4,4'-[(6-[4-(1,1-dimethyl)aminocarbonyl)phenylamino]-1,3, 5-triazine-2,4-diyl)diimino]-bis-(benzoic acid-2-ethyl-hexyl ester) (Uvasorb HEB)

3-(4'-methyl benzylidene)-d,l-camphor (Neo Heliopan®MBC)

3-benzylidene camphor salicylic acid-2-ethylhexyl ester (Neo Heliopan®OS)

4-dimethylaminobenzoic acid-2-ethylhexyl ester (Padimate O)

hydroxy-4-methoxybenzophenone-5-sulfonic acid and Na salt 2,2'-methylene bis-(6-(2H-benzotriazol-2-yl)-4-1,1,3,3-tetramethylbutyl)phenol) (Tinosorb®M)

phenylene bis-benzimidazyl tetrasulfonic acid disodium salt (Neo Heliopan®AP)

2,4-bis-[{(4-(2-ethylhexyloxy)-2-hydroxy}phenyl]-6-(4-methoxyphenyl)-1,3,5-triazine, (Tinosorb®S)

benzylidene malonate polysiloxane (Parsol®SLX)

menthyl anthranilate (Neo Heliopan®MA)

2-(4-diethylamino-2-hydroxybenzoyl)benzoic acid hexyl ester (Uvinul® A Plus)

indanylidene compounds in accordance with WO 02/38537

Products according to the present invention in the form of sunscreen formulations preferably have a SPF (sun protection factor) of equal or greater than 15, preferably of equal or greater than 20, more preferably of equal or greater than 30.

Preferred products of the present invention in the form of sunscreen formulations comprise 4-(1,1-dimethylethyl)-4'-methoxydibenzoylmethane (4-t-butyl-4'-methoxydibenzoyl methane; avobenzone), preferably in an amount in the range of from 0.2-10 wt.-%, more preferred in the range of from 0.5-5 wt.-%, based on the total weight of the sunscreen formulation.

In preferred sunscreen formulations comprising components (a) and (b) the pH-value is in the range of from pH 4 to pH 8, preferably from pH 4 to 6.5.

Products according to the present invention may comprise one or more compatible solutes. Preferred compatible solutes are described in WO 01/76572, namely dimyo-inositol phosphate (DIP), diglycerin phospate (DGP), di-myo-inositol phosphate (DIP), cyclic 2,3 diphosphoglycerate (cDPG), 1,1-di-glycerol phosphate (DGP), beta-mannosyl glycerate (firoin), beta-mannosyl glyceramide (firoin-A) and di-mannosyl-di-inositol phosphate (DMIP) and ectoine and ectoine-derivatives, as described in EP 0 553 884 A, EP 0 671 161 A and WO 94/15923, in particular ((S)-1,4,5,6-tetrahydro-2-methyl-4-pyrimidinecarboxylic acid) and hydroxyectoine ((S,S)-1,4,5,6-tetrahydro-5-hydroxy-2-methyl-4-pyrimidinecarboxylic acid).

Preferably, the total amount of compatible solutes is in the range of from 0.05 to 10 wt.-%, preferably 0.1 to 5 wt.-%, based on the total weight of the product according to the present invention.

Also preferred are products according to the present invention comprising one or more cooling agents selected from the group consisting of: menthol, preferably l-menthol, menthone glycerin acetal (trade name: Frescolat®MGA), menthyl lactate (preferably l-menthyl lactate, in particular l-menthyl-l-lactate, trade name: Frescolat®ML), substituted menthyl-3-carboxylic acid amide (e.g. menthyl-3-carboxylic acid-N-ethylamide), 2-isopropyl-N-2,3-trimethylbutanamide, substituted cyclohexane carboxylic acid amide, 3-menthoxypropane-1,2-diol, 2-hydroxyethylmenthylcarbonate, 2-hydroxypropylmenthylcarbonate, N-acetyl glycine menthyl ester, Isopulegol, menthyl hydroxycarboxylic acid ester (e.g. menthyl-3-hydroxybutyrate), monomenthyl-succinate, 2-mercaptocyclodecanone, menthyl-2-pyrrolidin-5-one carboxylate, 2,3-dihydroxy-p-menthane, 3,3,5-trimethyl cyclohexanone glycerine ketal, 3-menthyl-3,6-di- and -trioxa lkanoate, 3-menthylmethoxy acetate, N-(4-cyanomethylphenyl)-p-menthanecarboxamide, N-(4-cyanophenyl)-p-menthanecarboxamide and Icilin.

Preferred cooling agents are: l-menthol, menthone glycerine acetal (trade name: Frescolat®MGA), menthyl lactate (preferably l-menthyl lactate, in particular l-menthyl-l-lactate, trade name: Frescolat®ML), 3-menthoxy propane-1,2-diol, 2-hydroxyethyl menthyl carbonate, 2-hydroxypropyl menthyl carbonate, particular preference being for l-menthyl-l-lactate.

Products according to the present invention may comprise one or more anti-cellulite agents as well as agents enhancing or boosting the activity of anti-cellulite agents.

Anti-cellulite agents and lipolytic agents are preferably selected from the group consisting of those described in WO 2007/077541, and beta-adrenergic receptor agonists such as synephrine and its derivatives.

Agents enhancing or boosting the activity of anti-cellulite agents, in particular agents which stimulate and/or depolarise C nerve fibres, are preferably selected from the group consisting of capsaicin and derivatives thereof, vanillylnonylamid and derivatives thereof, L-carnitine, coenzym A, isoflavonoides, soy extracts, ananas extract and conjugated linoleic acid.

For certain products according to the present invention are preferred which in addition comprise one, two or more compounds of the group consisting of:

glycerol, 1,2-propanediol, 1,3-propanediol, 1,2-butanediol, 1,3-butanediol, 1,4-butanediol, 2,3-butanediol, 1,2-pentanediol, 1,5-pentanediol, 1,2-hexanediol, 1,6-hexanediol, 1,2-octanediol, 1,8-octanediol, 2-methylpentane-2,4-diol, 2,5-hexanediol, 3,6-octanediol, 2-ethyl-1,3-hexanediol, 1,3-octanediol, 1,2-decanediol, 1,3-decanediol, 1,2-dodecandiol, 1,2-tetradecandiol.

Products of the present invention in addition may additionally comprise known antimicrobials like chitosan, totarol, farnesol, glycerol monolaurate, arylalkyl alcohols, such as e.g. 4-methyl-4-phenyl-2-pentanol and its derivatives (DE 101 43 434, in particular 4-methyl-4-phenyl-2-pentanol), muguet alcohol (2,2-dimethyl-3-phenylpropanol), other arylalkyl alcohols (e.g. as disclosed in DE 44 47 361, DE 103 30 697, U.S. Pat. No. 4,110,430 or EP 1 157 687), 2-butyloctanoic acid, 2-hexyldecanoic acid, p-anisic acid, essential oils with antimicrobial properties and isolates from essential oils with antimicrobial properties like e.g. thymol or eugenol, perfume oils or single aroma chemicals with antimicrobial activity, polyglycerol esters, such as e.g. polyglyceryl 3-caprylates, or combinations of the substances mentioned, which are generally employed, inter alia, against underarm odor, foot odor, acne or dandruff formation.

In products of the present invention a combination with (metal) chelators is advantageous in some cases. (Metal) chelators which are preferably to be employed here are, inter alia, α-hydroxy fatty acids, phytic acid, lactoferrin, α-hydroxy acids, such as, inter alia, citric acid, lactic acid and malic acid, and humic acids, bile acids, bile extracts, bilirubin, biliverdin or EDTA, EGTA and derivatives thereof.

BRIEF DESCRIPTION OF DRAWINGS AND FIGURES

Figure 1:
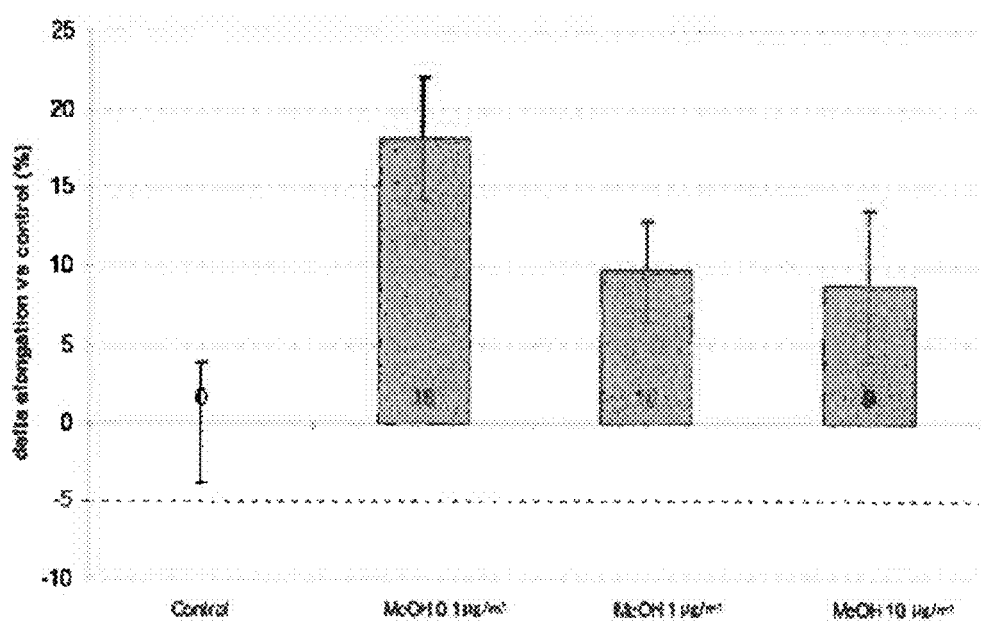
FIG. 1 shows the increase of hair follicles at day 10 of culture, expressed as percentage relative to an untreated control (modulation by dir-MeOH).

The invention is further described by the following figures and examples, without limiting the scope of the claims.

EXTRACTION EXAMPLE 1

Preparation of "Direct Extracts"

Tahitian *Isochrysis* CS 177 was used to prepare extracts by the following steps:
1. Prepare a suspension of powdery freeze-dried *Isochrysis* cell material in the selected extractant at a ratio (dry weight/volume) of 10 mg:1 ml;
2. stir the suspension in the dark at room temperature for 16 h;
3. centrifuge the suspension at 2000 g for 15 minutes to recover a supernatant and a cell material pellet;
4. resuspend the pellet in 0.5 ml of the aforementioned selected extractant for each ml used at the step 1;
5. immediately centrifuge the suspension at 2000 g for 15 minutes to recover a supernatant and a cell material pellet;
6. repeat steps 4 and 5 one more time;
7. combine the supernatants to form the "direct extract" of the respective extractant.

The extractant was chosen from water, methanol, ethanol, isopropanol, ethyl acetate and hexane:

TABLE 1

Ratio of dry extract/biomass (dry weight) with different extractants

| Extractant | % of the dried biomass |
|---|---|
| Water | 54 |
| Methanol | 47 |
| Ethanol | 38 |
| Iso-propanol | 24 |
| Ethyl acetate | 20 |
| Hexane | 12 |

EXTRACTION EXAMPLE 2

Preparation of "Sequential Extracts"

For preparation of "sequential extracts", first a direct extract was prepared. After step 6, the cell material pellet was resuspended in a selected further extractant, and steps 3 to 7 were then performed again with the selected further extractants.

A series of sequential extractions was produced according to table 2:

TABLE 2 sequential extracts and related ratio of extract/biomass in dry weight

| Version | Sequential protocol | Extractant | Extract symbol | % ratio dry extract/ biomass |
|---|---|---|---|---|
| 1 | Ethyl acetate followed by 30% ethanol | Ethyl acetate 30% ethanol | dir-EtAc seq. 30% EtOH | 20 |
| 2 | Methanol followed by water | methanol water | dirMeOH seq water2 | 47 15 |
| 3 | Hexane followed by ethyl acetate followed by ethanol followed by water | Hexane ethyl acetate Ethanol Water | dir-Hex seq-EtAc Seq-EtOH Seq-Water | 12 6 17 31 |
| 4 | Ethyl acetate followed by ethanol followed by water | Ethyl acetate Ethanol Water | dir-EtAc seq-EtOH2 seq-Water3 | 20 18 30 |
| 5 | Methanol followed by hexane/ ethyl acetate 1:1 (v/v) followed by water | methanol hexane/ethyl acetate 1:1 (v/v) water | dir-MeOH seq- Hex/EtAc Seq-Water4 | 47 3 7 |

EFFECTS EXAMPLES 1-3

Modulation of Hair Follicle Growth by dir-MeOH

These examples demonstrate the influence of the "direct methanol extract" according to extraction example 1 on hair follicle metabolism.

For each experiment and the control 9-12 follicles were used, plated at the density of 3 hair follicles/well in 24 well plates. Hair follicles were taken from the head of the scalp and transferred for cultivation in sterile 24 well plates using a modified Williams' Medium E. Cultivation took place for nine days, following 18 h of pre-incubation performed in order to select hair follicles suitable to be maintained in culture. Only those follicles showing a good vital stage and a growth of not less than 0.2 mm were used.

The growth performances observed in the treated hair follicles were compared to a control group, which was cultured in the same culture medium but free from extract supplement.

The experimental design consisted in treatments with dir-MeOH extract at three final concentrations corresponding to 0.1, 1 and 10 µg/ml; the concentrations were calculated in terms of extracted freeze-dried biomass. In order to obtain these supplemented media, the required quantity of dir-MeOH extract was submitted to solvent evaporation and then redissolved again in DMSO. The final concentration of this DMSO-solved extract has been adjusted in order to supplement the experimental media with the desired extract quantity, obtaining at same time a final concentration in DMSO equal to 0.05%. The same concentration of DMSO has also been used in the medium for the culture of the control group.

The activity of the microalgae treatment is demonstrated by the increase of hair follicle growth expressed as percentage variation in comparison to the elongation performed by the control group. The experiments were terminated after 10 days of cultivation (9 days of treatment). The growth of the hair follicles was studied by microphotography and subsequently determined by image analysis. All the hair follicles were photographed every two days.

The described experiment was replicated three times adopting hair follicles taken from 3 different donors. The results were pooled and combined into table 3 and FIG. 1, were the hair follicle elongation is expressed as percentage ratio between the experimental groups and the untreated control:

TABLE 3

Growth of hair follicles at day 10 of culture - Data pooled from three replicates
Elongation in [%] of the control performance ± standard error

| Ex. | Experimental treatment | Growth (%) | Standard error | No. of Hair follicles | ANOVA Test | DHA medium content wt. % | PUFAs medium content wt. % |
|---|---|---|---|---|---|---|---|
| 0 | Control | 100 | 3.8 | 28 | | — | — |
| 1 | dir-MeOH extr. 0.1 µg/ml | 118.1 | 3.9 | 25 | P < 0.01 | 0 | 0.01 |
| 2 | dir-MeOH extr. 1 µg/ml | 109.6 | 3.3 | 24 | n.s. | 0.02 | 0.06 |
| 3 | dir-MeOH extr. 10 µg/ml | 108.7 | 4.8 | 24 | n.s. | 0.24 | 0.56 |

DHA: docosahexaenoic acid, C22:6, the most prominent polyunsaturated fatty acid (PUFA)
PUFAs: DHA (C22:6), EPA (C20:5), stearidonic acid (C18:4), linolenic (C18:3) and linolic acid (C18:2)

The results are also shown in FIG. 1.

The results indicate that the addition of the dir-MeOH extract leads to a significant increase in growth of the hair follicles, varying from 9 to 18% in comparison to the untreated group. The most significant response has been obtained at the lower treatment which results highly significant also on a statistical basis (P<0.01).

EFFECTS EXAMPLES 4-5

Modulation of Hair Growth by dir-EtOH

The same experimental protocol described for the examples 1-3 has been repeated to investigate the activity of the direct ethanol extract with the exception that all the experimental groups and the control were prepared comprising 12-18 follicles.

Figure 2:
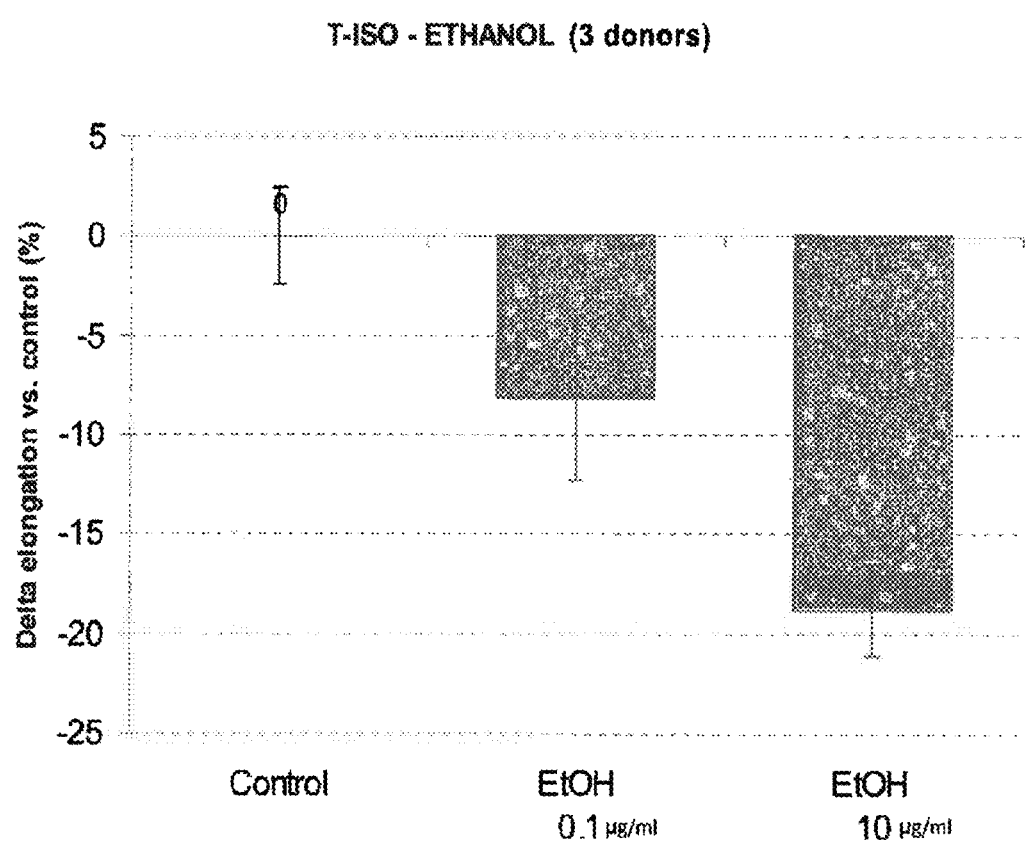
FIG. 2 shows the increase of hair follicles at day 10 of culture, expressed as percentage relative to an untreated control (modulation by dir-EtOH).

The following data has been obtained treating hair follicles taken from three different donors. Table 4 and FIG. 2 summarize the results.

TABLE 4

Growth of hair follicles at day 10 of culture - Data pooled from three replicates
Elongation in [%] of the control performance ± standard error

| Ex. | Experimental treatment | Growth (%) | Standard error | N. of Hair follicles | ANOVA Test | DHA medium content wt. % | PUFAs* medium content wt. % |
|---|---|---|---|---|---|---|---|
| 0 | Control | 100 | 2.4 | 44 | | — | — |
| 4 | dir-EtOH extr. 0.1 µg/ml | 91.9 | 4.2 | 30 | | 0 | 0.01 |
| 5 | dir-EtOH extr. 10 µg/ml | 81.2 | 2.4 | 31 | P < 0.01 | 0.28 | 0.87 |

*DHA (C22:6), EPA (C20:5), stearidonic acid (C18:4), linolenic (C18:3) and linolic acid (C18:2)

The results indicate that the addition of the EtOH extract leads to a significant reduction in growth of the hair follicles, varying from 8 to 19% in comparison to the untreated group. The most significant response has been obtained at the 10 μg/ml treatment, which results highly significant also on a statistical basis (P<0.01).

EFFECTS EXAMPLES 6-8

Modulation of Hair Growth by dir-EtAc

The same experimental protocol described for the effects examples 1-3 was repeated to investigate the activity of the direct ethyl acetate extract.

Figure 3:
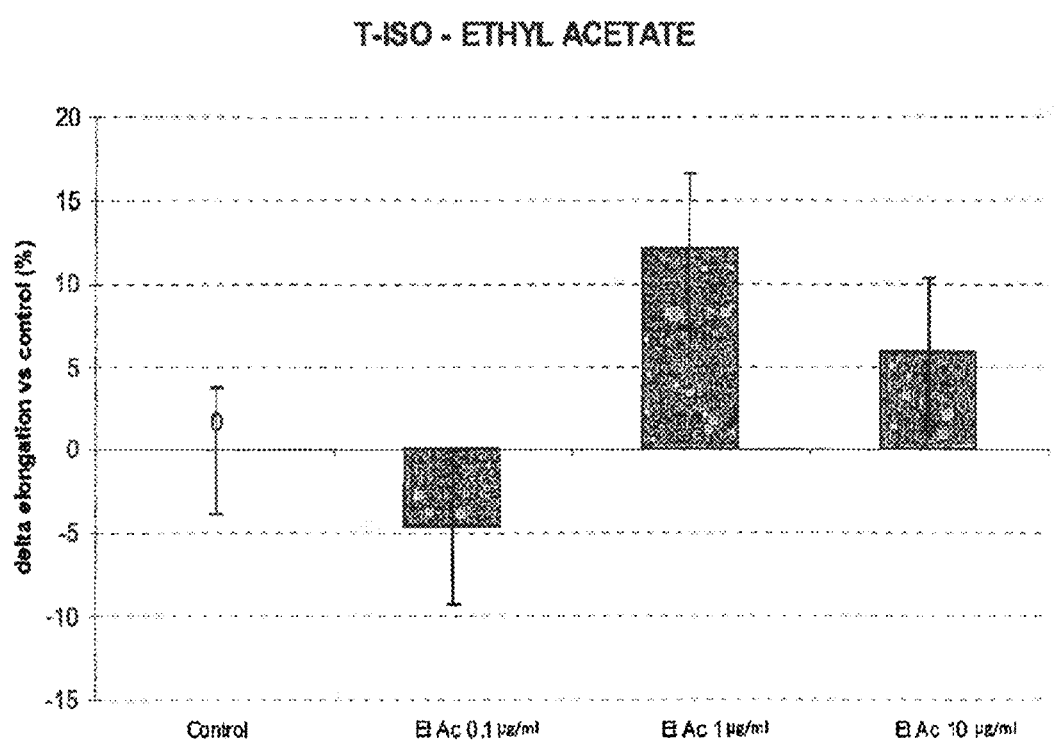
FIG. 3 shows the increase of hair follicles at day 10 of culture, expressed as percentage relative to an untreated control (modulation by dir-EtAc).

Table 5 and FIG. 3 summarize the results obtained by three replicate experiments using different donors:

TABLE 5

Growth of hair follicles at day 10 of culture - Data pooled from three replicates
Elongation in [%] of the control performance ± standard error

| Ex. | Experimental treatment | Growth (%) | Standard error | N. of Hair follicles | ANOVA Test | DHA medium content wt. % | PUFAs* medium content wt. % |
|---|---|---|---|---|---|---|---|
| 0 | Control | 100 | 3.8 | 28 | — | — | — |
| 6 | Dir-EtAc extract 0.1 μg/ml | 95.3 | 4.6 | 26 | n.s. | 0 | 0.01 |
| 7 | Dir-EtAc extract 1 μg/ml | 112.2 | 4.4 | 25 | P < 0.05 | 0.03 | 0.07 |
| 8 | Dir-EtAc extract 10 μg/ml | 105.9 | 4.5 | 26 | n.s. | 0.31 | 0.7 |

*DHA (C22:6), EPA (C20:5), stearidonic acid (C18:4), linolenic (C18:3) and linolic acid (C18:2)

The data show the effectiveness of the extract for modulation of the hair follicle growth. The treatment at middle concentration (1 μg/ml) produced a significant stimulation (P<0.05) of hair follicle growth equal to 12%, while increasing or reducing the treatment intensity the modulation become not significant.

EFFECTS EXAMPLES 9-20

Modulation of Hair Growth by Sequential Extracts

Figure 4:
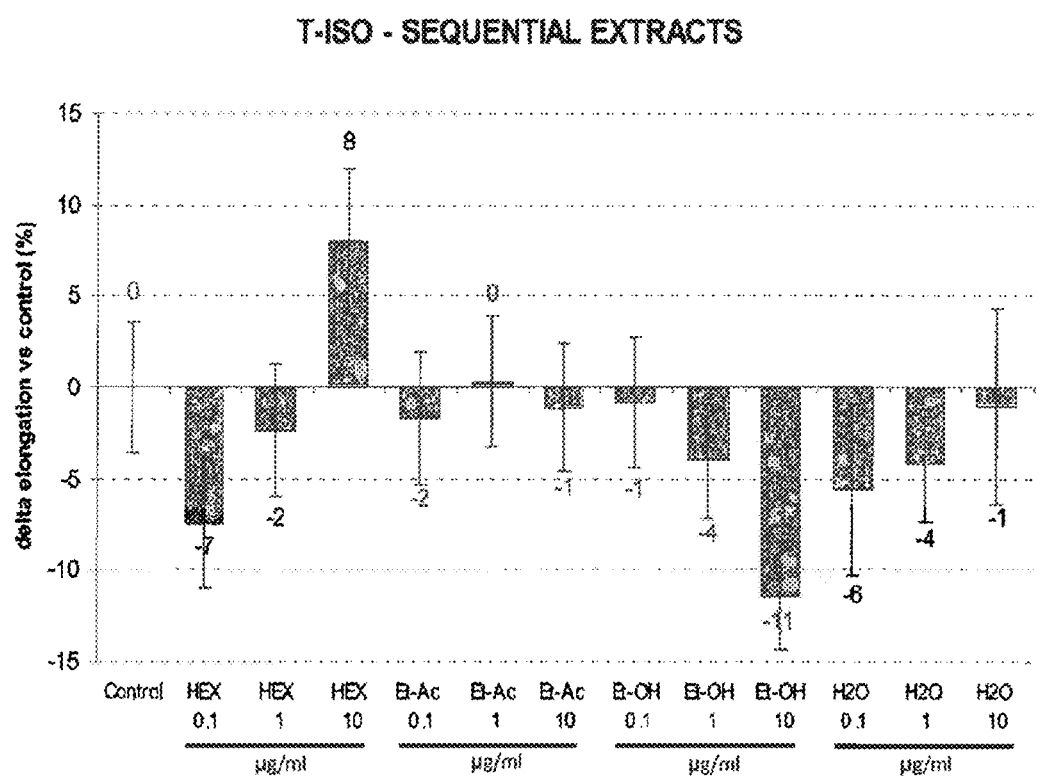
FIG. 4 shows the increase of hair follicles at day 10 of culture, expressed as percentage relative to an untreated control (modulation by sequential extracts).

"Sequential extracts" were prepared as described in extraction example 2. Four extracts were prepared (dir-HEX followed by seq-EtAc followed by seq-EtOH followed by seq-Water) and three dose treatments were tested for each of them. The experiment has been repeated three times using hair follicles obtained from different donors and the data have been pooled to represent the average response of the three donors. Table 6 and FIG. 4 summarize the results:

TABLE 6

Growth of hair follicles at day 10 of culture - Data pooled from three replicates
Elongation in [%] of the control performance ± standard error

| Ex. | Experimental treatment | Growth (%) | Standard error | N. of Hair follicles | ANOVA Test | DHA medium content wt. % | PUFAs* medium content wt. % |
|---|---|---|---|---|---|---|---|
| 0 | Control | 100 | 3.6 | 35 | | — | — |
| 9 | Dir-Hex extract 0.1 μg/ml | 92.5 | 3.6 | 34 | n.s. | 0 | 0.01 |
| 10 | Dir-Hex extract 1 μg/ml | 97.6 | 3.6 | 34 | n.s. | 0.03 | 0.06 |
| 11 | Dir-Hex extract 10 μg/ml | 108.0 | 4.0 | 34 | n.s. | 0.25 | 0.58 |
| 12 | Seq-EtAc extract 0.1 μg/ml | 98.3 | 3.6 | 34 | n.s. | 0 | 0 |
| 13 | Seq-EtAc extract 1 μg/ml | 100.3 | 3.6 | 31 | n.s. | 0 | 0.01 |
| 14 | Seq-EtAc extract 10 μg/ml | 98.9 | 3.5 | 30 | n.s. | 0.04 | 0.09 |
| 15 | Seq-EtOH extract 0.1 μg/ml | 99.2 | 3.6 | 32 | n.s. | 0 | 0 |
| 16 | Seq-EtOH extract 1 μg/ml | 96 | 3.1 | 34 | n.s. | 0 | 0 |
| 17 | Seq-EtOH extract 10 μg/ml | 88.6 | 2.9 | 30 | P < 0.05 | 0.02 | 0.03 |
| 18 | Seq-Water extract 0.1 μg/ml | 94.4 | 4.7 | 32 | n.s. | 0 | 0 |

TABLE 6-continued

Growth of hair follicles at day 10 of culture - Data pooled from three replicates
Elongation in [%] of the control performance ± standard error

| Ex. | Experimental treatment | Growth (%) | Standard error | N. of Hair follicles | ANOVA Test | DHA medium content wt. % | PUFAs* medium content wt. % |
|---|---|---|---|---|---|---|---|
| 19 | Seq-Water extract 1 µg/ml | 95.8 | 3.1 | 32 | n.s. | 0 | 0 |
| 20 | Seq-Water extract 10 µg/ml | 99 | 5.3 | 28 | n.s. | 0 | 0 |

*DHA (C22:6), EPA (C20:5), stearidonic acid (C18:4), linolenic (C18:3) and linolic acid (C18:2)

The experiments show that two classes of compounds active on hair growth have been separated in the sequential extracts: the first has been extracted by hexane and it produced a modulation of the hair growth changing from inhibiting to stimulating in response to the increasing intensity of treatment, while the second one is more hydrophilic and has been extracted by seq-ethanol. This latter produced a significant inhibition of the hair follicle growth ($P<0.05$) at 10 µg/ml.

EFFECTS EXAMPLES 21-26

Modulation of Hair Growth by Direct Hexane Extracts

Figure 5:
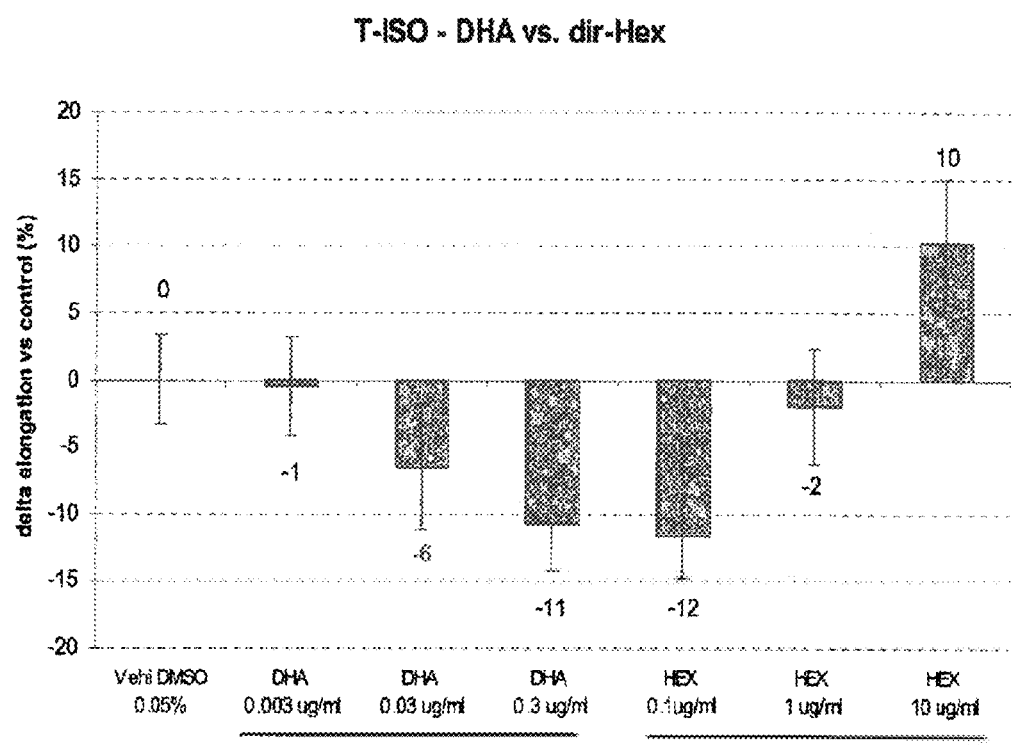
FIG. 5 shows the increase of hair follicles at day 10 of culture, expressed as percentage relative to an untreated control (modulation by dir-Hex).

Direct hexane extract were prepared as described in Extraction Example 1 to investigate the activity of the direct extract obtained using hexane in comparison with the activity of pure DHA (docosahexaenoic acid, C22:6). The aim of the experiment was to verify that the action of the dir-Hex is reproducible by treatment with DHA that is highly represented among the PUFAs synthesised by Isochrysis sp., in particular Tahitian Isochrysis. Since it has been detected that the dir-Hex extract is constituted of DHA for about 20%, it has been estimated that a treatment with dir-Hex at 0.1 µg/ml corresponds to treat hair follicles with 0.02 µg/ml of DHA. In order to reproduce a treatment balanced around this value three groups of hair follicles were cultured in medium culture supplemented with DHA ranging from 0.003 to 0.3 µg/ml and they have been compared with others treated with dir-Hex ranging from 0.1 to 10 µg/ml, as usual. In order to supplement the culture medium with DHA, docosahexaenoic acid was solved in DMSO at concentrations suitable to arrive at the final content of 0.05% DMSO in the medium. The experiment has been repeated twice and the pooled results are summarised in Table 7 and FIG. 5.

The results show that DHA produced an inhibiting dose-response, while the dir-Hex inhibited hair follicle growth at low concentration (i.e. low DHA) and stimulated the growth at higher concentrations (i.e. increasing DHA content). These data confirm that DHA and dir-Hex treatments produce different effects on hair follicle growth and the dir-Hex activity cannot be explained by DHA content.

EFFECTS EXAMPLES 27-30

Modulation of Hair Pigmentation by dir-EtAc and seq-30% EtOH

The activity on pigmentation of both lipophilic (dir-EtAc) and hydrophilic (seq-30% EtOH) extracts obtained from Tahitian Isochrysis has been studied by performing an experiment with a biological sample taken from a single donor. The culture media for the experimental treatments were prepared according to the previous Extraction Examples, in order to obtain the following experimental treatments:

1) dir-EtAc=0.1 µg/ml and 1 µg/ml;

2) seq-30% EtOH=0.1 µg/ml and 10 µg/ml.

Figure 6:
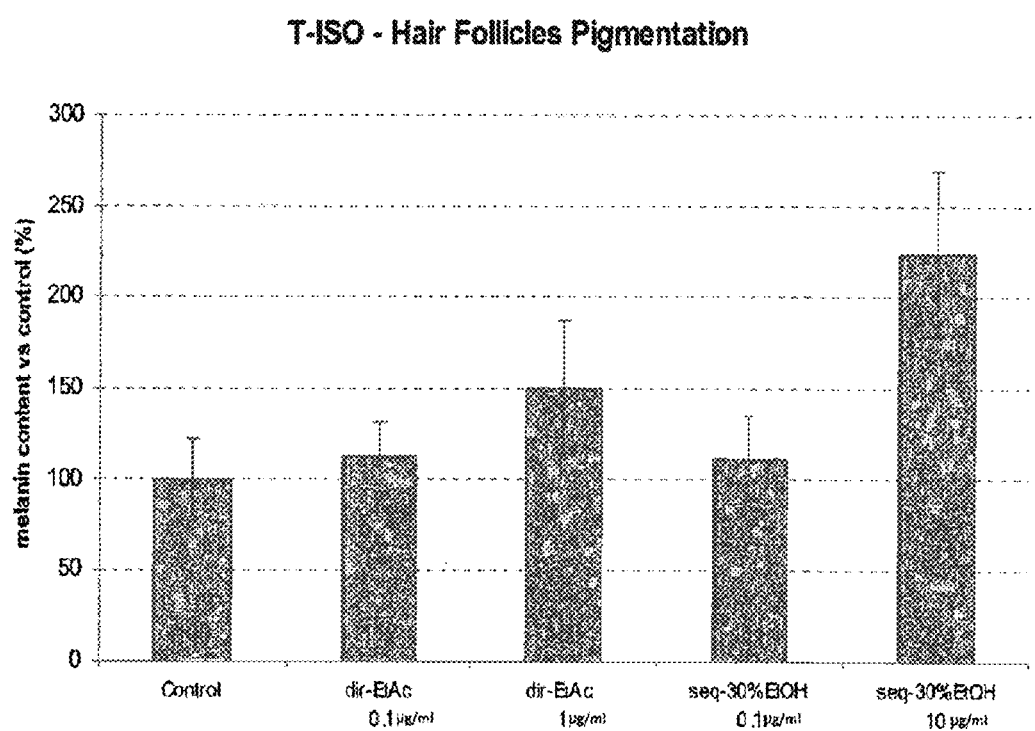
FIG. 6 shows the increase of hair follicle melanin content at day 10 of culture, expressed as percentage relative to an untreated control (modulation by dir-EtAc and SEQ-30% EtOH).

The hair follicles culture was terminated after 5 days of cultivation (4 of treatment). Subsequently, hair follicles were subjected to histological analysis by preparing sections stained according to Fontana Masson technique. The melanin content of the tissues surrounding dermopapillas was detected by image analysis and the results are shown in Table 8 and FIG. 6.

TABLE 7

Growth of hair follicles at day 10 of culture - Data pooled from two donors
Elongation in [%] of the control performance ± standard error

| Ex. | Experimental treatment | Growth (%) | Standard error | N. of Hair follicles | ANOVA Test | DHA medium content wt. % | PUFAs medium content wt. % |
|---|---|---|---|---|---|---|---|
| 0 | Control | 100 | 3.3 | 30 | | — | — |
| 21 | DHA 0.003 µg/ml | 99.5 | 3.6 | 19 | | | |
| 22 | DHA 0.03 µg/ml | 93.5 | 4.7 | 18 | | | |
| 23 | DHA 0.3 µg/ml | 89.3 | 3.5 | 19 | $P < 0.05$ | | |
| 24 | Dir-Hex extract 0.1 µg/ml | 88.4 | 3.2 | 19 | $P < 0.05$ | 0 | 0.01 |
| 25 | Dir-Hex extract 1 µg/ml | 98 | 4.3 | 19 | | 0.03 | 0.06 |
| 26 | Dir-Hex extract 10 µg/ml | 110.1 | 4.8 | 19 | | 0.25 | 0.58 |

TABLE 8

Melanin content of hair follicles at day
5 of culture - Data from single donor
Melanin content in [%] of the control performance ± standard error

| Ex. | Experimental Treatment | Melanin content (%) | Standard error | N. of Samples | ANOVA Test |
|---|---|---|---|---|---|
| 0 | Control | 100 | 21.5 | 12 | |
| 27 | dir-EtAc 0.1 μg/ml | 112.3 | 18.7 | 12 | |
| 28 | dir-EtAc 1 μg/ml | 149.8 | 36.8 | 12 | |
| 29 | seq-30% EtOH 0.1 μg/ml | 111.4 | 22.8 | 12 | |
| 30 | seq-30% EtOH 10 μg/ml | 223.5 | 45.7 | 12 | P < 0.01 |

The results clearly indicate that the treatment of hair follicles with the microalgae extracts increased the content of melanin after 4 days of treatment. The intensity of the response varies with the dose. However, the more intensive responses have been detected by treating with seq-30% EtOH extract at 10 μg/ml (highly significant; P<0.01) and dir-Et-Ac extract at 1 μg/ml.

EFFECTS EXAMPLES 31-42

Modulation of Hair Pigmentation by Sequential Extracts

The experiment on hair follicle pigmentation has been repeated using four-step sequential extracts (hexane followed by ethyl acetate followed by ethanol followed by water) prepared by treating the *Isochrysis* biomass as previously described in Extraction Example 2.

The culture techniques and histological analysis were the same described for Effects Examples 27-30.

Figure 7:
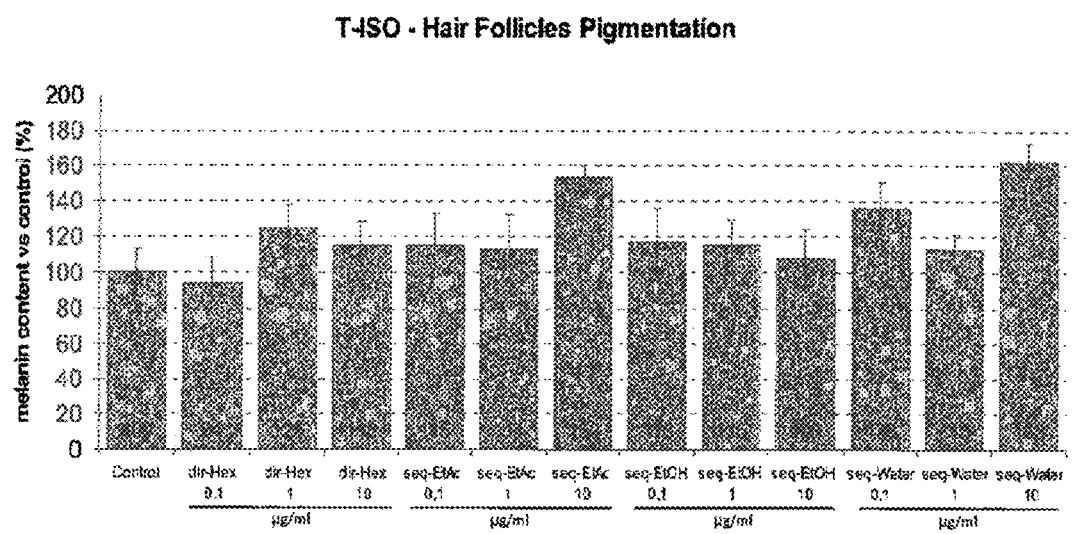
FIG. 7 shows the increase of hair follicle melanin content at day 10 of culture, expressed as percentage relative to an untreated control (modulation by sequential extract).

The culture media for the experimental treatments were prepared according to the previous descriptions, in order to obtain the following experimental treatments:
1) dir-Hexane=0.1-1-10 μg/ml;
2) seq-EtAc=0.1-1-10 μg/ml;
3) seq-EtOH=0.1-1-10 μg/ml;
4) seq-water=0.1-1-10 μg/ml;
The results are shown in Table 9 and FIG. 7:

TABLE 9

Melanin content of hair follicles at day
5 of culture - Data from single donor
Melanin content in [%] of the control performance ± standard error

| Ex. | Experimental Treatment | Melanin content (%) | Standard error | N. of Samples | ANOVA Test |
|---|---|---|---|---|---|
| 0 | Control | 100 | 13.3 | 12 | |
| 31 | dir-Hex 0.1 μg/ml | 93.7 | 14.5 | 12 | |
| 32 | dir-Hex 1 μg/ml | 125 | 13.3 | 12 | |
| 33 | dir-Hex 10 μg/ml | 114.8 | 13.8 | 12 | |
| 34 | seq-EtAc 0.1 μg/ml | 115.4 | 17.8 | 12 | |
| 35 | seq-EtAc 1 μg/ml | 113.6 | 18.9 | 12 | |
| 36 | seq-EtAc 10 μg/ml | 153.3 | 6.8 | 12 | P < 0.05 |
| 37 | seq-EtOH 0.1 μg/ml | 117.6 | 18.3 | 12 | |
| 38 | seq-EtOH 1 μg/ml | 115.3 | 14.3 | 12 | |
| 39 | seq-EtOH 10 μg/ml | 108.1 | 16 | 12 | |
| 40 | seq-Water 0.1 μg/ml | 136 | 14.6 | 12 | |
| 41 | seq-Water 1 μg/ml | 112.8 | 9 | 12 | |
| 42 | seq-Water 10 μg/ml | 163.2 | 9.8 | 12 | P < 0.01 |

The results point out a general pigmentation enhancement in response to experimental treatments, with statistically significant results for 10 μg/ml seq-EtAc (ANOVA=P<0.05) and 10 μg/ml seq-water (ANOVA=P<0.01).

EFFECTS EXAMPLES 43-50

Modulation of Skin Pigmentation by Sequential Extracts

Organ culture of full thickness human skin has been performed starting from a skin sample, exciding pieces of about 4×4 mm and culturing them up to day 6. The culture medium was a modified William-E and it has been changed at the day 3.

Samples of the sequential extracts as described by Extraction Example 2 were air-dried and then redissolved in a quantity of DMSO suitable to obtain a final concentration of 1 and 10 μg/ml. The experimental treatments were daily replicated applying 5 ul of extract, solved in pure DMSO, on the surface of the cultured skin samples.

Figure 8:
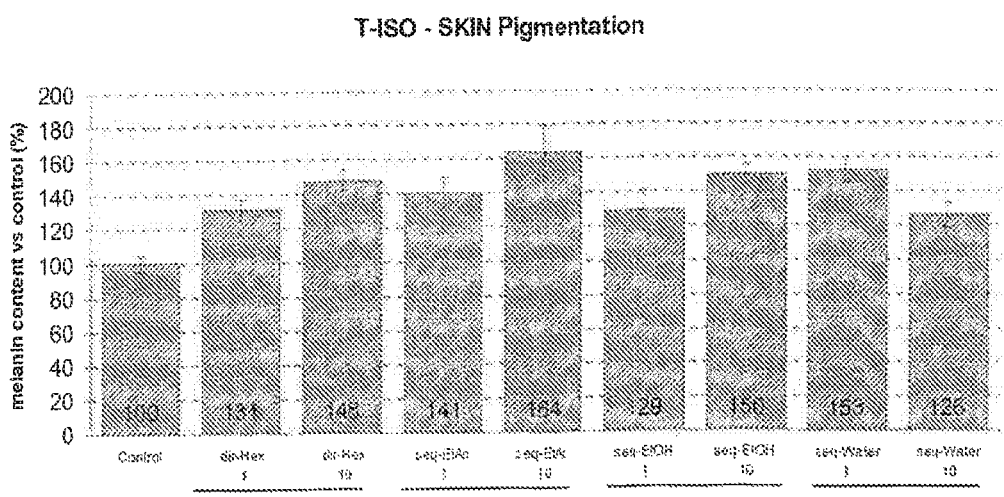
FIG. 8 shows the increase in skin pigmentation at day 10 of culture, expressed as percentage relative to an untreated control (modulation by sequential extracts).

After six days of organ culture, histological section were prepared from the skin samples and the quantitative changes of melanin content have been investigated following Fontana-Masson staining technique. The melanin quantification was obtained by image analysis of microphotographs of each histological skin section. Table 10 and FIG. 8 summarize the results:

TABLE 10

Melanin content of skin at day 6 of
culture - Data from single donor
Melanin content in [%] of the control performance ± standard error

| Ex. | Experimental Treatment | Melanin content (%) | Standard error | N. of Samples | ANOVA Test |
|---|---|---|---|---|---|
| 0 | Control | 100 | 4.8 | 12 | |
| 43 | dir-Hex 1 μg/ml | 131.1 | 6.3 | 12 | P < 0.05 |
| 44 | dir-Hex 10 μg/ml | 147.6 | 6.3 | 12 | P < 0.01 |
| 45 | seq-EtAc 1 μg/ml | 140.6 | 8.8 | 12 | P < 0.05 |
| 46 | seq-EtAc 10 μg/ml | 163.9 | 15.1 | 12 | P < 0.01 |
| 47 | seq-EtOH 1 μg/ml | 129.2 | 12 | 12 | P < 0.05 |
| 48 | seq-EtOH 10 μg/ml | 149.7 | 6 | 12 | P < 0.01 |
| 49 | seq-Water 1 μg/ml | 153 | 7.5 | 12 | P < 0.01 |
| 50 | seq-Water 10 μg/ml | 126.3 | 7.3 | 12 | P < 0.05 |

In this experiment all the treatments produced a significant (ANOVA=P<0.05) increase of the skin melanin content. The treatments with dir-Hex 10 μg/ml, seq-EtAc 1-10 μg/ml, seq-EtOH 10 μg/ml and seq-Water 1 μg/ml stimulated statistically highly significant responses (ANOVA=P<0.01).

The effects resulted in general in more intense pigmentation than in hair follicles, however, also in this case the more relevant responses have been recorded by treating the tissue with seq-EtAc (10 μg/ml) and seq-Water (1 μg/ml) extracts.

EFFECTS EXAMPLES 51-54

Modulation of Skin Pigmentation by dir-EtOH

The same protocol described for previous examples 43-50 has been adopted in the following experiment planned to investigate the activity on skin pigmentation related to dir-EtOH extract according to Extraction Example 1.

Figure 9:
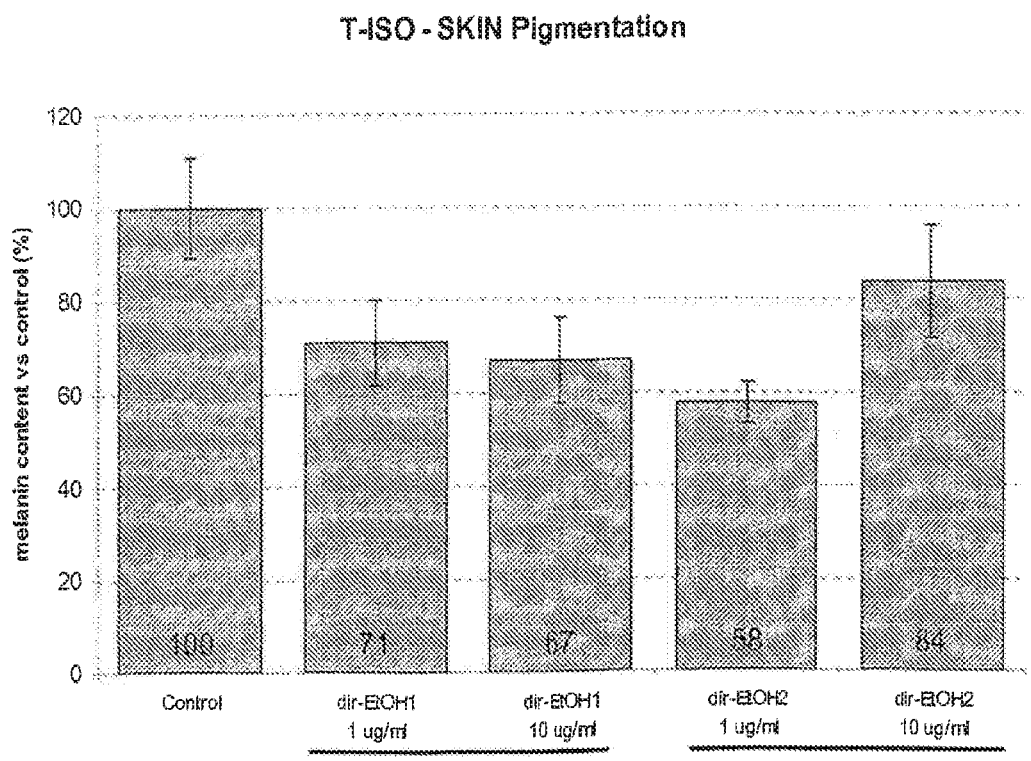
FIG. 9 shows the increase of skin pigmentation at day 10 of culture, expressed as percentage relative to an untreated control (modulation by dir-EtOH).

The extract preparation has been performed using two samples of Tahitian *Isochrysis* biomass, obtained from two different cultivations of the same algal strain. In order to compare the performance of the two extracts, they have been labelled as dir-EtOH1 and dir-EtOH2. Table 11 and FIG. 9 show the results:

TABLE 11

Melanin content of skin at day 6 of culture - Data from single donor
Melanin content in [%] of the control performance ± standard error

| Ex. | Experimental Treatment | Melanin content (%) | Standard error | N. of Samples | ANOVA Test |
|---|---|---|---|---|---|
| 0 | Control | 100 | 10.8 | 8 | |
| 51 | dir-EtOH1 1 μg/ml | 70.9 | 9.2 | 6 | |
| 52 | dir-EtOH1 10 μg/ml | 67.1 | 9.1 | 8 | P < 0.05 |
| 53 | dir-EtOH2 1 μg/ml | 57.8 | 4.4 | 8 | P < 0.01 |
| 54 | dir-EtOH2 10 μg/ml | 83.8 | 12.1 | 8 | |

The results show that both dir-EtOH extracts inhibited the pigmentation, in contrast to the stimulation detected using the extracts obtained with different extractants. Both samples of Tahitian *Isochrysis* showed the same effects despite that they originated from different cultures. All responses were inhibiting and dir-EtOH1 at 10 μg/ml produced a response significant on statistical basis (P<0.05) while dir-EtOH2 gave a very significant response at 1 μg/ml (P<0.01).

This means that different actives are present in *Isochrysis* sp., preferably Tahitian *Isochrysis*, biomass and they can be separated by choosing the appropriate solvent.

EFFECTS EXAMPLES 55-62

Modulation of Skin Pigmentation by dir-EtOH and "Sequential Extracts"

The same protocol described for previous Effects Examples 51-54 was adopted in an experiment designed to compare the activity of dir-EtOH with some "sequential extracts" according to Extraction Example 2. The aim of the experiment also was to confirm presence of different actives in Tahitian *Isochrysis* biomass and the possibility to separate them by using different solvents.

Figure 10:
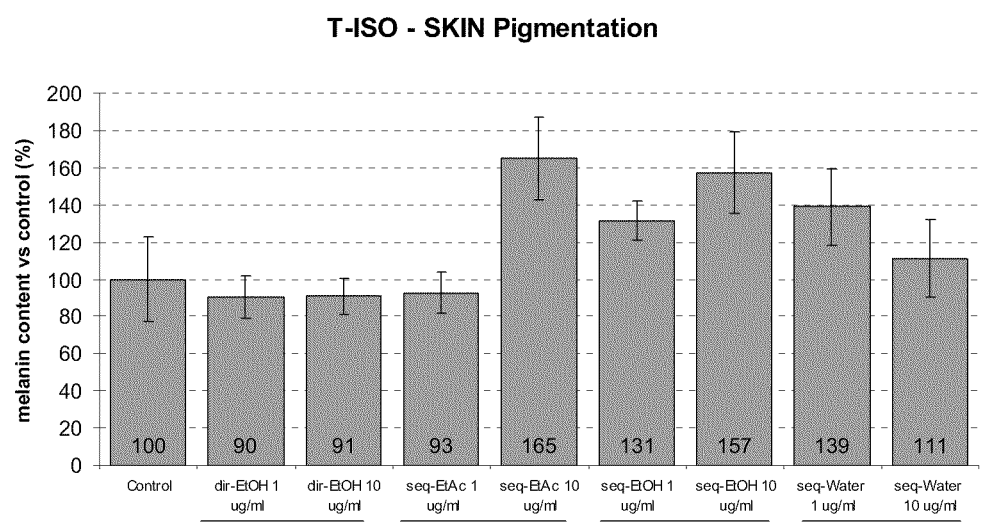
FIG. 10 shows the increase of skin pigmentation at day 10 of culture, expressed as percentage relative to an untreated control (comparison of dir-EtOH and sequential extracts).

The extracts included in the experiment and obtained results are showed in Table 12 and FIG. 10:

TABLE 12

Melanin content of skin at day 6 of culture - Data from single donor
Melanin content in [%] of the control performance ± standard error

| Ex. | Experimental Treatment | Melanin content (%) | Standard error | N. of Samples | ANOVA Test |
|---|---|---|---|---|---|
| 0 | Control | 100 | 22.3 | 8 | |
| 55 | dir-EtOH 1 μg/ml | 90.3 | 11.5 | 8 | |
| 56 | dir-EtOH 10 μg/ml | 90.7 | 10 | 8 | |
| 57 | seq-EtAc 1 μg/ml | 92.7 | 11.2 | 8 | |
| 58 | seq-EtAc 10 μg/ml | 164.9 | 22.1 | 8 | P < 0.01 |
| 59 | seq-EtOH 1 μg/ml | 131.5 | 10.5 | 8 | |
| 60 | seq-EtOH 10 μg/ml | 157.3 | 21.6 | 8 | P < 0.05 |
| 61 | seq-Water 1 μg/ml | 138.8 | 20.5 | 8 | |
| 62 | seq-Water 10 μg/ml | 111.2 | 21 | 8 | |

The results are consistent with the expectations: dir-EtOH tended to inhibit pigmentation, while seq-EtOH produced a significant stimulation (P<0.05). Seq-EtAc (P<0.01) and seq-Water again stimulated the melanin synthesis as expected (see Effects Examples 45-50).

EFFECTS EXAMPLES 63-65

Modulation of Hair Growth by Sequential Extracts

A "sequential extract" was prepared as described in extraction example 2. Two extracts were prepared (dir-MeOH followed by seq-Hex/EtAc) and a three dose treatment was tested for the seq-Hex/EtAc extract. The experiment has been repeated four times using hair follicles taken from 4 different donors and the data have been pooled to represent the average response of the four donors. Table 13 summarizes the results of the seq-Hex/EtAc extract:

TABLE 13

Growth of hair follicles at the day 9 of culture - Data pooled from four replicates
Elongation in [%] of the control performance ± standard error

| Ex. | Experimental Treatment | Growth (%) | Standard error | N. of Hair follicles | ANOVA Test |
|---|---|---|---|---|---|
| 0 | Control | 100 | 2.6 | 62 | |
| 63 | Seq-Hex/EtAc 0.1 μg/ml | 104.4 | 2.6 | 43 | n.s. |
| 64 | Seq-Hex/EtAc 1 μg/ml | 112.0 | 3.0 | 44 | P < 0.01 |
| 65 | Seq-Hex/EtAc 10 μg/ml | 101.9 | 3.4 | 41 | n.s. |

The results attest that the addition of the seq-Hex/EtAc extract leads to a significant increase in growth of the hair follicles, in comparison to the untreated group. The most significant response has been obtained by treating at the dosage of 1 µg/ml which results highly significant also on a statistical basis (P<0.01).

The seq-Hex/EtAc dry extract only contained trace amounts of PUFAs (<0.2 wt. %).

EFFECTS EXAMPLES 66-67

Modulation of Skin Pigmentation by "Sequential Extracts"

The same protocol described for previous Effects Examples 51-54 was adopted in an experiment designed to determine the activity of a "sequential extract" according to Extraction Example 2. Two extracts were prepared (dir-MeOH followed by seq-Hex/EtAc) and a three dose treatment of the seq-Hex/EtAc extract was tested.

The results are showed in Table 14:

TABLE 14

Melanin content of skin at the day 6 of culture - Data from single donor
Melanin content in [%] of the control performance ± standard error

| Ex. | Experimental Treatment | Melanin content (%) | Standard error | N. of Samples |
|---|---|---|---|---|
| 0 | Control | 100 | 13.7 | 8 |
| 66 | Seq-Hex/EtAc 1 µg/ml | 131.3 | 13.0 | 8 |
| 67 | Seq-Hex/EtAc 10 µg/ml | 110.1 | 11.4 | 8 |

In this experiment both treatments produced an increase of melanin content. The treatment with 1 µg/ml led to an increase of about 30% in melanin content.

PRODUCT EXAMPLES 1-11

Skin Care

In table 1 means

1=Skin tanning "water-in-oil" emulsion

2=Skin tanning "oil-in-water" emulsion with UVA/B broadband protection

3=Skin tanning and hair growth inhibiting "oil-in-water" cream

4=Hair growth inhibiting aerosol foam with UVB/UVA protection

5=Skin lightening and hair growth inhibiting cream O/W

6=Skin tanning moisturizing balm

7=Skin tanning body spray O/W

8=Skin lightening and hair growth inhibiting gel

9=Skin tanning and hair growth inhibiting soaking liquid for wipes

10=Hair growth inhibiting and hair lightening antiperspirant pump spray

11=Skin lightening non-aerosol foam

TABLE 1

| RAW MATERIAL NAME (SUPPLIER) | INCI | 1 | 2 | 3 | 4 | 5 | 6 | 7 | 8 | 9 | 10 | 11 |
|---|---|---|---|---|---|---|---|---|---|---|---|---|
| | | | | | | | PPM | | | | | |
| Tahitian Isochrysis dry extract | Isochrysis Extract | | | | | | 10 | 25 | | | | |
| Tahitian Isochryis extract (dry extract content 1 wt %) | Maltodextrin. Isochrysis Extract | | | 50 | 500 | | | | | | 100 | |
| Isochrysis extract (dry extract content 0.2 wt %) | Glycerin, Water (Aqua), Pentylene Glycol, Isochrysis Extract | 500 | | | | | | | 100 | | | 150 |
| Tahitian Isochryis extract (dry extract content 1 wt %) | 1,2-Pentyleneglycol, Isochrysis Extract | 10 | | | | 200 | | | 300 | | | |
| | | | | | | WEIGHT % | | | | | | |
| Abil 100 ® (Goldschmidt) | Dimethicone | | 2.0 | | 0.5 | | | | | | | 1.0 |
| Alugel 34 TH (Baerlocher) | Aluminium Stearate | 1.0 | | | | | | | | | | |
| alpha-Bisabolol (Symrise) | Bisabolol | 0.1 | | 0.1 | | 0.2 | 0.1 | | 0.1 | 0.1 | 0.1 | 0.1 |
| Aristoflex AVC (Clariant) | Ammonium Acryloyldimethyl-taurate/VP Co-polymer | | | | | | | | 0.8 | | | |

TABLE 1-continued

| RAW MATERIAL NAME (SUPPLIER) | INCI | 1 | 2 | 3 | 4 | 5 | 6 | 7 | 8 | 9 | 10 | 11 |
|---|---|---|---|---|---|---|---|---|---|---|---|---|
| Beta-Arbutin | Arbutin | | | | | | | | | | | 0.2 |
| Butylene Glycol | Butylene Glycol | | | | | | | | | 10.0 | | |
| Caffeine | Caffeine | | | 0.2 | | | | 0.3 | | | | |
| Carbopol Ultrez-10 (Noveon) | Carbomer | | | | | | | | | 0.5 | | |
| Carbopol 2050 ® (B.F. Goodrich) | Carbomer | | | 0.1 | 0.1 | | | | | | | |
| Cetiol OE (Cognis) | Dicaprylyl Ether | | | | | | | | | | | 3.0 |
| Citric Acid 10% solution | Citric Acid | | | | | | | | | 0.75 | | |
| Corapan TQ ® (Symrise) | Diethylhexyl-1,6-Naphtalate | | 3.0 | | | | | | | | | |
| Dihydroxyacetone (Merck) | Dihydroxyacetone | | | | | | | | 2.0 | 2.0 | | |
| D-Panthenol (BASF) | Panthenol | | | | | | | | 0..5 | | | 0..5 |
| Dow Corning 345 Fluid | Cyvlomethicone | | | | | | | 0.5 | | | | |
| Dragocare W (Symrise) | PEG-40 Butyloctanol Wheat Germ Esters, Water (Aqua), Lactic Acid, Tocopherol | | | | | | | | | 1.0 | | |
| Dragocid Liquid (Symrise) | Phenoxyethanol (and) Methylparaben (and) Ethylparaben (and) Butylparaben (and) Propylparaben (and) Isobutylparaben | 1.0 | 0.3 | 0.8 | 0.3 | | | | | | | 0.3 |
| Dragosan W/O P (Symrise) | Sorbitan Isostearate, Hydrogenated Castor Oil, Ceresin, Beeswax (Cera Alba) | 7.0 | | | | | | | | | | |
| Dracorin CE | Glyceryl Stearate Citrate | | | | | 5.0 | | | | | | |
| Dracorin GMS (Symrise) | Glyceryl Stearate | | | 2.0 | 2.0 | | | | | | | |
| Dracorin GOC (Symrise) | Glyceryl Oleate Citrate, Caprylic/Capric Triglyceride | | | | | | | 2.0 | | | | |
| Drago-Oat-Active | Water (Aqua), Butylene Glycol, *Avena Sativa* (Oat) Kernel Extract | | | | | | | | | 1.0 | | |
| Dragoxat 89 (Symrise) | Ethylhexyl Isononanoate | | | | | | | 5.0 | 3.0 | 2.0 | | |
| Dragoxat EH (Symrise) | Ethylhexyl Ethylhexanoate | | | 3.0 | | 3.0 | | | | | | |
| Edeta BD ® (BASF) | Dinatrium-EDTA | | 0.1 | | 0.1 | 0.1 | 0.1 | | | | | 0.1 |
| Emulgade PL | Cetearyl Glucoside, Cetearyl Alcohol | | | 0.5 | | | | | | | | |
| Emulsiphos (Symrise) | Cetylphosphate, Hydrogenated Palm glycerides | | | 2.0 | 1.5 | | | | | | | |
| Ethanol (96%) | Alcohol Denat. | | | | | 2.0 | | | | 60.0 | | |
| Extrapone *Aloe Vera* (Symrise) | Glyerin, Water (Aqua), *Aloe Barbadensis* Leaf Extract | 3.0 | | | | | | | | 0.5 | | |

TABLE 1-continued

| RAW MATERIAL NAME (SUPPLIER) | INCI | 1 | 2 | 3 | 4 | 5 | 6 | 7 | 8 | 9 | 10 | 11 |
|---|---|---|---|---|---|---|---|---|---|---|---|---|
| Extrapone Chamomile (Symrise) | Glycerin, Water (Aqua), *Chamomilla Recutica* (*Matricaria*), Flower Extract | | | 0.5 | | | | | | | | |
| Extrapone Green Tea (Symrise) | Glycerin, Water (Aqua), *Cemallia Sinensis* Leaf Extract | | | 0.2 | | | | | | | | |
| Extrapone Rosemary (Symrise) | Glycerin, Water (Aqua), *Rosmarinus Officinalis* (Rosemary) Leaf Extract | | | 0.3 | | | | | | | | |
| Extrapone Witch Hazel (Symrise) | Propylene Glycol, *Hamamelis Virginiana* (Witch Hazel) Water, Water (Aqua), *Hamamelis Virginiana* (Witch Hazel) Extract | 1.0 | | | | | | | | | | |
| Fragrance | Parfum (Fragrance) | 0.4 | 0.5 | 0.3 | 0.4 | 0.3 | 0.3 | 0.2 | 0.2 | 0.5 | 1.0 | 0.2 |
| Glycerin 99% | Glycerin | 2.0 | 4.0 | 2.0 | 3.0 | 1.5 | | | 5.0 | | | 4.0 |
| Hostacerin DGMS ® (Clariant) | Polyglceryl-2-Stearate | | 3.0 | | | | | | | | | |
| Hydrolite-5 (Symrise) | 1,2-Pentyleneglycol | | | | 3.5 | 5.0 | 5.0 | | | 1.0 | 5.0 | 5.0 |
| Hydroviton 24 (Symrise) | Water (Aqua), Pentylene Gylcol, Glycerin, Sodium Lactate, Lactic Acid, Serine, Urea, Sorbitol, Sodium Chloride, Allantoin | | | | | | | | | | 1.0 | |
| Isodragol (Symrise) | Triisononanoin | | | 2.0 | | | | | | | | |
| Isopropylmyristat (Symrise) | Isopropyl Myristate | | | | | 4.0 | | | | | | |
| Karion F (Merck) | Sorbitol | 2.0 | | | | | | | | | | |
| Keltrol T ® (Calgon) | Xanthan Gum | | 0.2 | 0.1 | | 0.3 | | | | | | |
| Kojic acid | Kojic acid | | | | | 0.2 | | | | | | |
| Lanette E ® (Cognis) | Natriumcetearylsulfat | | 0.7 | | | | | | | | | |
| Lanette O ® (Cognis) | Cetearyl Alcohol | | | 3.0 | | | | | | | | |
| Lanette 16 ® (Cognis) | Cetyl alcohol | | 2.0 | | 0.5 | 1.0 | | | | | | |
| Lara Care A-200 (Rahn) | Galactoarabinan | | | | | | | | | | | 0.2 |
| Locron L (Cognis) | Aluminium Chlorohydrate | | | | | | | | | | 16.0 | |
| Magnesium Sulfat Hepathydrat (Merck) | Magnesium Sulfate | 0.7 | | | | | | | | | | |
| Mineral Oil | Paraffinum Liquidum | | | | | | | | 4.0 | | | |
| NaOH 10% aq. solution | Sodium hydroxide | | 0.2 | | 2.9 | | | 0.4 | 1.0 | | | 0.6 |
| Neo Heliopan ® AP (Symrise), 15% as sodium salt | Dinatrium-Phenyldibenzimi-dazoltetrasulfonate | | 6.7 | | | | | | | | | |
| Neo Heliopan ® AV (Symrise) | Ethylhexylmethoxy-cinnamate | | | | 6.0 | | | | | | | 2.0 |

TABLE 1-continued

| RAW MATERIAL NAME (SUPPLIER) | INCI | 1 | 2 | 3 | 4 | 5 | 6 | 7 | 8 | 9 | 10 | 11 |
|---|---|---|---|---|---|---|---|---|---|---|---|---|
| Neo Heliopan ® BB (Symrise) | Benzophenone-3 | | | | | | 0.25 | | | | | |
| Neo Heliopan ® 357 (Symrise) | Butyl Methoxy-dibenzoyl-methane | | 0.6 | | 1.5 | | | | | | | 1.5 |
| Neo Heliopan ® E 1000 (Symrise) | Isoamyl-p-methoxycinnamate | | | | | | | | | | | 6.0 |
| Neo Heliopan ® HMS (Symrise) | Homosalate | | 9.5 | | | | | | | | | |
| Neo Heliopan ® Hydro (15% aq. solution neutralized with NaOH) (Symrise) | Phenylbenzimidazol sulfonic acid | | 6.7 | | 13.3 | | | | | | | |
| Neo Heliopan ® MBC (Symrise) | 4-Methylbenzyliden-campher | | | | 4.0 | | | | | | | 3.0 |
| Neo-PCL Water Soluble N (Symrise) | Trideceth-9, PEG-5 Ethyl-hexanoate, Water (Aqua) | | | | | | | | 1.0 | | 2.0 | |
| Neutral oil (Symrise) | Caprylic/Capric Triglyceride | | 5.0 | 0.25 | 2.0 | 6.0 | | 4.0 | | | | |
| PCL liquid 100 (Symrise) | Cetearyl Ethyl-hexanoate | 12.0 | | 5.0 | | 3.0 | 3.0 | 7.0 | | | | |
| PCL solid (Symrise) | Stearyl Heptanoate, Stearyl Caprylate | | | 2.0 | | | 1.5 | | | | | |
| Pemulen TR-2 (Noveon) | Acrylates/C10-30 Alkyl Acrylate Crosspolymer | | | | | | | | 0.2 | | | 0.2 |
| Phenoxyethanol (Symrise) | Phenoxyethanol | | 0.7 | | 0.7 | | | | | | | 0.7 |
| Prisorine 3505 ® (UniQema) | Isostearic acid | | 0.5 | | | | | | | | | |
| 1,2-Propylenglycol | Propylene Glycol | | | 5.0 | | | | | 5.0 | | 3.0 | |
| Sepigel 305 | Polyacrylamide, C13-14 Isoparaffin, Laureth-7 | | | | | | 1.0 | | | | | |
| SF1214 ® (Bayer) | Cyclopentasiloxane, Dimethicone | | 1.0 | | | | | | | | | |
| Solubilizer (Symrise) | PEG-40 Hydrogenated Castor Oil, Trideceth-9, Propylene Glycol, Water (Aqua) | | | | | | | | 1.0 | 1.75 | 3.0 | |
| Sun Flower Oil (H. Erhard Wagner) | Helianthus Annus (Sunflower) Seed Oil | 5.0 | | | | | | | | | | |
| Sweet Almon Oil (H. Erhard Wagner) | Prunus Dulcis | 5.0 | | | | | | | | | | |
| SymDeo MPP (Symrise) | Dimethyl Phenyl 2-Butanol | | | | | | | | | | 0.5 | |
| Symdiol 68 (Symrise) | 1,2-Hexanediol, Caprylalcohol | | 0.5 | | | | | | 0.5 | | | |
| SymGlucan (Symrise) | Water, Glycerin, Beta-Glucan | | | 0.3 | | | | | | | | |
| SymWhite 377 (Symrise) | Phenylethyl Resorcinol | | | | | | 0.2 | | | | | |
| Tegosoft TN ® (Goldschmidt) | C12-C15 Alkyl-benzoate | | 2.0 | | 2.0 | | | | | | | |

TABLE 1-continued

| RAW MATERIAL NAME (SUPPLIER) | INCI | 1 | 2 | 3 | 4 | 5 | 6 | 7 | 8 | 9 | 10 | 11 |
|---|---|---|---|---|---|---|---|---|---|---|---|---|
| Texapon N 70 (Cognis) | Sodium Laureth Sulfate | | | | 0.1 | 0.5 | | | | | | 0.5 |
| Vitamin E Acetate (DSM Nutritional Products) | Tocopheryl Acetate | 3.0 | 0.5 | | 0.5 | | | | | | | 0.5 |
| Vitamin A Palmitate in oil (1 Miole/g) (DSM Nutritional Products) | Retinyl Palmitate | 0.2 | | | | | | | | | | |
| Water, demineralized | Aqua (Water) | ad 100 | ad 100 | ad 100 | ad 100 | ad 100 | ad 100 | ad 100 | ad 100 | ad 100 | ad 100 | ad 100 |

PRODUCT EXAMPLES 12-20

Hair Care

In table 2 means
12=Hair growth stimulating tonic
13=2 in 1 After sun shampoo with hair tanning properties
14=Hair tanning conditioner with UVB/UVA protection
15=Liquid hair leave-on, pump-foam with hair growth stimulating properties
16=Hair growth stimulating styling gel
17=Hair growth inhibiting and hair lightening setting foam
18=Mascara with hair growth stimulating and hair tanning properties
19=Hair growth stimulating anti-dandruff shampoo
20=Hair growth inhibiting leave-on hair conditioner
21=Hair tanning and hair growth stimulating shampoo Table 2:

| RAW MATERIAL NAME (SUPPLIER) | INCI | 12 | 13 | 14 | 15 | 16 | 17 | 18 | 19 | 20 | 21 |
|---|---|---|---|---|---|---|---|---|---|---|---|
| | | PPM | | | | | | | | | |
| Tahitian Isochrysis dry extract | Isochrysis Extract | | 25.0 | | | | | | | 10.0 | |
| Isochryis extract (dry extract content 0.5 wt %) | Maltodextrin, Isochrysis Extract | | | | | 20 | 100 | | | | |
| Isochrysis extract (dry extract content 2 wt %) | Propylene Glycol, Water (Aqua), PEG-40 Hydrogenated Castor Oil, Trideceth-9, Isochrysis Extract | 25 | | 500 | | | | | 150 | | |
| Tahitian Isochryis extract (dry extract content 1 wt %) | 1,2-Pentyleneglycol, Water (Aqua), Isochrysis Extract | | | | 100 | | 200 | | | | 500 |
| | | WEIGHT % | | | | | | | | | |
| Abil B 9950 (Evonic Goldschmidt) | Dimethicone Propyl Pg-Betaine | | | | | 0.2 | | | | | |
| Abil-Quat 3272 (Evonic Goldschmidt) | Quaternium-80 | | | | | 0.5 | | | | | |
| Actipone AlphaPulp (Symrise) | Water (Aqua), Butylene Glycol, Malic Acid, Actinidia Chinensis (Kiwi) Fruit Juice, Citrus Aurantium Dulcis (Orange) | | | | | 0.75 | | | | | |

| RAW MATERIAL NAME (SUPPLIER) | INCI | 12 | 13 | 14 | 15 | 16 | 17 | 18 | 19 | 20 | 21 |
|---|---|---|---|---|---|---|---|---|---|---|---|
| | Juice, Citrus Paradisi (Grapefruit) Juice, Pyrus Malus (Apple) Juice, Trideceth-9, Prunus Amygdalus Dulcis (Sweet Almond) Seed Extract | | | | | | | | | | |
| Aloe Vera Gel Concentrate 10/1 (Symrise) | Water (Aqua), Aloe Barbadensis Leaf Juice | | 0.5 | | | | | | | 0.5 | |
| -(-Alpha-)-Bisabolol, natural (Symrise) | Bisabolol | | | | | | | | 0.1 | | |
| Aminexil | Diaminopyrimidine Oxide | 0.3 | | | | | | | | | |
| Antil 141 Liquid (Evonic Goldschmidt) | Propylene Glycol, PEG-55 Propylene Glycol Distearate | | 1.0 | | | | | | | | |
| Antil 171 (Evonic Goldschmidt) | PEG-18 Glyceryl Oleate/Cocoate | | | | | | | | 2.0 | | |
| Caffeine | Caffeine | 0.5 | | 0.1 | | | | | | | 0.3 |
| Carbopol Ultrez-10 (Noveon) | Carbomer | | | | | 0.7 | | | | | |
| Celquat L-200 (National Starch & Chemical) | Polyquaternium-4 | | | | 1.0 | | | | | | |
| CeramideBio | N-(1-Hexadecanoyl)-4-hydroxy-L-prolin-(1-hexadecyl-ester | | | 0.2 | | | | | | | |
| Citric Acid 10% solution | Citric Acid | | | 1.3 | 1.6 | | | | | | q.s. |
| Colour (Symrise) | Colour | | | | | | | | 0.2 | | |
| Crinipan AD (Symrise) | Climbazole | | | | | | | | 0.5 | | |
| Crotein Q (Croda) | Hydroxypropyl Trimonium Hydrolyzed Collagen | | | 1.0 | | | | | | | |
| Dehyquart A CA (Cognis) | Cetrimonium Chloride | 0.2 | 1.0 | | 4.0 | | | | | 4.0 | |
| Dehyquart SP (Cognis) | Quaternium-52 | | | 0.5 | | | | | | | |
| Dehyton K (Cognis) | Cocamidopropyl Betaine | | 8.0 | | | | 0.5 | | | | 2.0 |
| Dermosaccharides GY (Impag) | Water (Aqua), Glycerin, Glycogen | | | | 1.0 | | | | | | |
| D-Panthenol 75L (DSM Nutritional) | Panthenol | 0.5 | 1.0 | | 0.5 | | | | | | |
| Dow Corning 245 Fluid | Cyclopentasiloxane | | | | | | | 5.0 | | | |
| Dow Corning 5225C Formulation Aid | Cyclopentasiloxane, PEG/PPG-18/18 Dimethicone | | | | | | | 1.0 | | | |
| Dracorin GMS (Symrise) | Glyceryl Stearate | | | | | | | 2.0 | | | |
| Dragocide Liquid (Symrise) | Phenoxyethanol, Methyl-, Ethyl-, Butyl-, Propyl-, Isobutylparaben | | 0.8 | 0.5 | | 0.5 | | | 0.7 | 0.8 | 0.5 |

-continued

| RAW MATERIAL NAME (SUPPLIER) | INCI | 12 | 13 | 14 | 15 | 16 | 17 | 18 | 19 | 20 | 21 |
|---|---|---|---|---|---|---|---|---|---|---|---|
| Dragocolor Blue (Symrise) | Basic Blue 99 | | | | | | | | | | 0.02 |
| Dragocolor Brown (Symrise) | Basic Brown 17 | | | | | | | | | | 0.1 |
| Dragocolor Mahagony (Symrise) | Basic Brown 16 | | | | | | | | | | 0.1 |
| Dragoderm (Symrise) | Glycerin, Triticum Vulgare (Wheat) Gluten, Water (Aqua) | | 1.0 | | | | | | | 2.0 | |
| Edeta BD (BASF) | Disodium EDTA | | | | | | | 0.05 | | | |
| Emulgin B2 (Cognis) | Ceteareth-20 | | | 0.7 | | | | | | | |
| Ethanol 96% | Ethanol | 48.0 | | | 3.0 | 5.0 | 13.0 | | | | |
| Euperlan PK 771 (Cognis) | Glycol Distearate, Sodium Laureth Sulfate, Cocamide MEA, Laureth-10 | | | | | | | | 3.0 | | |
| Euperlan PK 900 BENZ-W (Cognis) | PEG-3 Distearate | | | | | | | | | | 2.0 |
| Euperlan PK 4000 (Cognis) | Glycol Distearate, Laureth-4, Cocoamidopropyl Betaine | | 2.5 | | | | | | | | |
| Ewacera 12 (H. Erhard Wagner) | Bees Wax | | | | | | | 10.0 | | | |
| Ewacera 34 (H. Erhard Wagner) | Carnauba Wax | | | | | | | 4.0 | | | |
| Extrapone Camomile (Symrise) | Water (Aqua), Propylene Glycol, Butylene Glycol, Chamomilla Recutita (Matricaria) Flower Extract, Glucose, Bisabolol | | | | | | | | 0.5 | | |
| Extrapone Green Tea GW (Symrise) | Glycerin, Water (Aqua), Camellia Sinensis Leaf Extract | | | | | | | | 0.3 | | |
| Extrapone Hop GW | Glycerin, Water (Aqua), Humulus Lupulus (Hops) Cone Extract, Glucose | 0.4 | | | | | | | | | |
| Extrapone Lemongrass (Symrise) | Propylene Glycol, Water (Aqua), PEG-40 Hydrogenated Castor Oil, Trideceth-9, Cymbopogon Citratus Leaf Oil, Lactic Acid | 0.4 | | | | | | | | 1.0 | |
| Extrapone Rosemary GW (Symrise) | Glycerin, Water (Aqua), Rosmarinus officinalis (Rosemary) Leaf Extract | | 0.3 | | | | | | | | |
| Fragrance (Symrise) | Fragrance | 0.5 | 0.3 | 0.4 | 0.2 | 0.4 | 0.5 | | 0.5 | 0.3 | 0.4 |
| Frescolat ML (Symrise) | Menthyl Lactate | 0.5 | | | | 0.8 | | | 0.5 | | |
| Glycerin, 99.5% | Glycerin | | | | | 10.0 | | | | | |
| Hydrolite-5 (Symrise) | Pentylene Glycol | | | | 0.5 | | | | | | |
| Keltrol T (Calgon) | Xanthan Gum | | | | | | | 0.15 | | | |

-continued

| RAW MATERIAL NAME (SUPPLIER) | INCI | 12 | 13 | 14 | 15 | 16 | 17 | 18 | 19 | 20 | 21 |
|---|---|---|---|---|---|---|---|---|---|---|---|
| Lanette 18 (Cognis) | Stearyl Alcohol | | | | | | | 2.0 | | | |
| Lanette O (Cognis) | Cetearyl Alcohol | | | 2.5 | | | | | | 3.5 | |
| Luviskol K 30 (BASF) | PVP | | | | 2.0 | | | | | | |
| Luviskol K 30 Powder (BASF) | PVP/Polyvinylpyrrolidone | | | | | 3.0 | | 4.0 | | | |
| Luviskol VA 64 Powder (BASF) | PVP/VA Copolymer | | | | | | 4.0 | | | | |
| MBD 210 20% Dispersion | Carbon Black, Water (Aqua) | | | | | | | 5.0 | | | |
| Minoxidil | Minoxidil | | | | | 0.5 | | | | | |
| Merquat 550 (Ondeo) | Polyquaterinium-7 | | 1.0 | | | | | | | | |
| Mulsifan RT 203/80 (Z&S) | C12-15 Pareth-12 | | | | | 4.0 | | | | | |
| Neo Heliopan 357 (Symrise) | Butyl Methoxy-dibenzoylmethane | | | 0.5 | | | | | | | |
| Neo Heliopan BB (Symrise) | Benzophenone-3 | 0.1 | 0.2 | | | | | | 0.3 | | |
| Neo Heliopan E 1000 (Symrise) | Isoamyl-p-methoxy-cinnamate | | | | 2.0 | | | | | | |
| Neo-PCL Water soluble N (Symrise) | Trideceth-9, PEG-5 Ethyl-hexanoate, Water (Aqua) | | | | 1.0 | | | | | | |
| Neutrol TE (BASF) | Tetrahydroxypropyl Ethylendiamine | | | | | 1.4 | | | | | |
| Niacinamide | Niacinamide | 0.2 | | | | | | | | | |
| Permethyl 104A (Cesham) | Polyisobutene C68 | | | | | | | 1.0 | | | |
| Plantacare 1200 UP (Cognis) | Lauryl glucoside | | | | | | | | | | 10.0 |
| Polymer JR 400 (Nordmann, Rassmann) | Polyquaternium-10 | | | | | | | | 0.2 | | |
| Polyquart H 81 (Cognis) | PEG-15 Coco Polyamine | | | | | | | | | 3.0 | |
| Potassium Sorbate | Potassium Sorbate | | | | | 0.2 | | | | | |
| Prestige Sparkling Pure Gold (Eckart) | Mica, Titanium Dioxide, Iron Oxides | | | | | | | 3.0 | | | |
| Propane Butane 4,2 Bar | Propane-Butane | | | | | | 10.0 | | | | |
| 1,2-Propylenglycol | Propylene Glycol | | | | | | | 2.0 | | | |
| Rose CL forte (Symrise) | Water (Aqua), Glycerin, PEG-40 Hydrogenated Castor Oil, Rosa Damascena Flower Oil | | | 0.5 | | | | | | | |
| Seanamin FP LS 5988 (Impag) | Hydrolyzed Actin, Water (Aqua), Glycerin, Fucus Vesiculosus Extract | | | | 1.0 | | | | | | |
| Sodium Benzoate | Sodium Benzoate | | | | 0.5 | | | | | | |
| Sodium Chloride | Sodium Chloride | | | 0.5 | | | | | 2.0 | 2.0 | |
| Sodium Hydroxide, 10% sol. | Sodium Hydroxide | | | 0.1 | | | | | | | |
| Solubilizer (Symrise) | PEG-40 Hydrogenated Castor Oil, Trideceth-9, Water (Aqua) | 1.0 | | | | | | | | | |
| Stearic Acid (Cognis) | Stearic Acid | | | | | | | 2.0 | | | |

-continued

| RAW MATERIAL NAME (SUPPLIER) | INCI | 12 | 13 | 14 | 15 | 16 | 17 | 18 | 19 | 20 | 21 |
|---|---|---|---|---|---|---|---|---|---|---|---|
| Tego Betain 810 (Evonic Goldschmidt) | Capryl/Capramidopropyl Betaine | | | | 0.5 | | | | | | |
| Texapon K 14 S Special (Cognis) | Sodium Myreth Sulfate | | | | | | | | 12.0 | | |
| Texapon N 70 (Cognis) | Sodium Laureth Sulfate | | 10.0 | | | | | | 12.0 | | |
| Triethanolamine | Triethanolamine | | | | | | | 0.5 | | | |
| Veegum HV | Magnesium Aluminium Silicate | | | | | | | 0.55 | | | |
| Water, demineralized | Wasser (Aqua) | Ad 100 | Ad 100 | Ad 100 | Ad 100 | Ad 100 | Ad 100 | ad 100 | Ad 100 | Ad 100 | Ad 100 |

PRODUCT EXAMPLES 22-34

Beauty from Inside

Gelatine Capsule for Direct Consumption

| RAW MATERIAL NAME | WEIGHT % | | |
|---|---|---|---|
| | 22 | 23 | 24 |
| Gelatine shell: | | | |
| Glycerin | 2.014 | 2.014 | 2.014 |
| Gelatine 240 Bloom | 7.91 | 7.91 | 7.91 |
| Sucralose | 0.065 | 0.065 | 0.065 |
| Allura Red | 0.006 | 0.006 | 0.006 |
| Brillant Blue | 0.005 | 0.005 | 0.005 |
| Core composition: | | | |
| Plant oil triglyceride (coconut oil fraktion) | ad 100 | ad 100 | ad 100 |
| Aroma B | 9.95 | 12.0 | 12.0 |
| Tahitian *Isochrysis* dry extract | | 0.005 | 0.01 |
| *Isochrysis* extract (plant oil triglyceride:dry extract 95:5 (w/w)) | 0.02 | | |

Aroma B had the following composition (figures in wt. %): 0.1% neotame powder, 0.05% aspartame, 29.3% peppermint oil arvensis, 29.3% peppermint piperita oil Willamette, 2.97% sucralose, 2.28% triacetin, 5.4% diethyl tartrate, 12.1% peppermint oil yakima, 0.7% ethanol, 3.36% 2-hydroxyethyl menthyl carbonate, 3.0% 2-hydroxypropyl menthyl carbonate, 0.27% vanillin, 5.5% D-limonene, 5.67% L-menthyl acetate.

The gelatine capsule suitable for direct consumption (produced in an analogous way to WO 2004/050069) had a diameter of 5 mm and the weight ratio of core material to shell material was 90:10. The capsule opened in the mouth in less than 10 seconds and dissolved completely in less than 50 seconds.

| Compressed tablets | | | |
|---|---|---|---|
| RAW MATERIAL NAME | WEIGHT % | | |
| | 25 | 26 | 27 |
| Magnesium stearate (as lubricant) | 0.9 | 0.9 | 0.9 |
| Citric acid | 0.2 | 0.2 | 0.2 |
| *Isochrysis* dry extract | 0.01 | 0.005 | 0.001 |
| Dextrose | Ad 100 | Ad 100 | Ad 100 |

Preparation instructions: Mix all the constituents and press to a compressed product in a suitable machine.

| Chewing gums | | |
|---|---|---|
| RAW MATERIAL NAME | WEIGHT % | |
| | 28 | 29 |
| Chewing gum base | 21.0 | 30.0 |
| Glycerin | 0.5 | 1.0 |
| Menthol spearmint aroma | 1.0 | 0.7 |
| Glucose syrup | 16.5 | |
| Icing sugar | Ad 100 | |
| Tahitian *Isochrysis* dry extract | | 0.01 |
| *Isochryis* extract (maltodextrin:dry extract 99:1 (w/w)) | 0.5 | |
| Sorbitol, powdered | | Ad 100 |
| Palatinite | | 9.5 |
| Xylitol | | 2.0 |
| Mannitol | | 3.0 |
| Aspartame | | 0.1 |
| Acesulfame K | | 0.1 |
| Emulgum/emulsifier | | 0.3 |
| Sorbitol 70%, in water | | 14.0 |

In table 3 means
30=Instant beverage mix
31=Sugar-free instant beverage mix
32=Carbonated soft drink
33=Soja-fruit drink
34=Low-fat yoghurt

TABLE 3

| RAW MATERIAL NAME | WEIGHT % | | | | |
|---|---|---|---|---|---|
| | 30 | 31 | 32* | 33 | 34 |
| Tahitian *Isochrysis* dry extract | | 0.005 | 0.007 | | 0.01 |

TABLE 3-continued

| RAW MATERIAL NAME | WEIGHT % | | | | |
|---|---|---|---|---|---|
| | 30 | 31 | 32* | 33 | 34 |
| Isochryis extract (maltodextrin:dry extract 95:5 (w/w)) | 0.2 | | | 0.02 | |
| Sugar (sucrose) | ad 100 | | | | |
| Citric acid | 4.00 | 33.33 | 0.2 | | |
| Trisodium citrate | 0.26 | | | | |
| Tricalcium phosphate | 0.22 | | | | |
| Ascorbic acid (vitamin C) | 0.24 | 0.44 | | | |
| Clouding agent and titanium dioxide (E 171) | 0.20 | | | | |
| Xanthan gum (E 415) | 0.072 | | | | |
| Sodium carboxy methyl cellulose (E 467) | 0.064 | | | | |
| Pectin (E 440) | 0.04 | | | | |
| Spray-dried pineapple flavor, including yellow colorant tartrazine | 0.40 | | | | |
| Spray-dried raspberry flavor, including red colorant | | 11.50 | | | |
| Lemon and lime flavor | | | 0.01 | | |
| D-Limonene | | | 0.005 | | |
| Maltodextrin (powder) | | ad 100 | | | |
| Aspartame | | 3.30 | | | |
| Saccharose | | | 8.0 | 6.0 | 5.0 |
| Hesperetin (1 wt. % in 1,2-propylene glycol) | | | 0.05 | | |
| Phloretin (1 wt. % in 1,2-propylene glycol) | | | 0.05 | | |
| Ethylhydroxymethyl-furanone | | | 0.01 ppb | | |
| Vanilla flavor | | | | 0.10 | 0.125 |
| Vanillin | | | 15 ppb | | |
| Maltol | | | 350 ppb | | |
| 2,5-Dimethyl-4-hydroxy-2H-furan-3-one | | | 3 ppb | | |
| 1,2-Propylene glycol | | | 0.1 | | |
| Mixture of fruit juice concentrates | | | | 45.0 | |
| Soja powder | | | | 5.0 | |
| Yoghurt (1.5 wt. % fat) | | | | | ad 100 |
| Water | | | ad 100 | ad 100 | |

*Carbonated after filling into bottles.

It is claimed:

1. A method for promoting pigmentation of hair and/or skin in a human subject in need thereof, comprising topically applying to the hair and/or skin of the subject a composition comprising an effective amount of an extract of Tahitian *Isochrysis*, wherein the extract of Tahitian *Isochrysis* is obtained by the method consisting essentially of the following steps:
    (i) cultivating Tahitian *Isochrysis* sp. cells;
    (ii) harvesting the cultivated Tahitian *Isochrysis* cells to obtain completely or substantially intact cell material;
    (iii) optionally, washing and/or freeze-drying the completely or substantially intact cell material to provide a washed and/or freeze-dried cell material;
    (iv) extracting the completely or substantially intact cell material or the washed and/or freeze-dried cell material with a solvent selected from the group consisting of hexane, ethyl acetate, ethanol, water, methanol, isopropanol, and a combination thereof for up to 24 h at a temperature of not more than 50° C. to provide an extract and extracted cell material; and
    (v) separating the extract from the extracted cell material, and
    wherein the composition is a cosmetic, dermatological, or therapeutic composition selected from the group consisting of a sunscreen composition, a self-tanning composition, a shaving composition, an after-shave, a deodorant, an antiperspirant, a shampoo, a conditioner, a hair tonic, a hair lotion, a hair rinse, a styling cream, a hair-setting composition, a styling aid, a blonding composition, a hair-coloring composition, or a decorative cosmetic.

2. The method of claim 1, wherein the solvent in step (iv) is at least one of hexane, ethyl acetate, water, and methanol.

3. The method of claim 1, wherein step (iv) occurs in the dark and/or under agitation.

4. A method for promoting pigmentation of hair and/or skin in a human subject in need thereof, comprising orally administering to the subject a composition comprising an effective amount of an extract of Tahitian *Isochrysis*, wherein the extract of Tahitian *Isochrysis* is at least one of a hexane, ethyl acetate, ethanol, water, methanol or isopropanol extract of Tahitian *Isochrysis* sp., wherein the extract is obtained by the method consisting essentially of the following steps:
    (i) cultivating Tahitian *Isochrysis* sp. cells;
    (ii) harvesting the cultivated Tahitian *Isochrysis* cells to obtain completely or substantially intact cell material;
    (iii) optionally, washing and/or freeze-drying the completely or substantially intact cell material to provide a washed and/or freeze-dried cell material;
    (iv) extracting the completely or substantially intact cell material or the washed and/or freeze-dried cell material with a solvent selected from the group consisting of hexane, ethyl acetate, ethanol, water, methanol, isopropanol, and a combination thereof for up to 24 h at a temperature of not more than 50° C. to provide an extract and extracted cell material; and
    (v) separating the extract from the extracted cell material, and
    wherein the composition in a form selected from the group consisting of a tablet, a dragee, a capsule, juice, a solution, granules and a foodstuff.

5. The method of claim 4, wherein step (iv) occurs in the dark and/or under agitation.

6. The method of claim 4, wherein the solvent in step (iv) is at least one of hexane, ethyl acetate, water, and methanol.

* * * * *